US010668257B2

(12) United States Patent
Broyles et al.

(10) Patent No.: US 10,668,257 B2
(45) Date of Patent: Jun. 2, 2020

(54) BLOW MOLDED COMPOSITE DEVICES AND METHODS

(71) Applicant: W. L. Gore & Associates, Inc., Newark, DE (US)

(72) Inventors: Michael R. Broyles, Flagstaff, AZ (US); Edward H. Cully, Flagstaff, AZ (US); Peter Heicksen, Flagstaff, AZ (US); Joseph B. Koenig, Flagstaff, AZ (US); Matthew E. Maulding, Bellemont, AZ (US); Kenneth Mazzarese, Rancho Mission Viejo, CA (US)

(73) Assignee: W. L. Gore & Associates, Inc., Newark, DE (US)

(*) Notice: Subject to any disclaimer, the term of this patent is extended or adjusted under 35 U.S.C. 154(b) by 470 days.

(21) Appl. No.: 14/882,330

(22) Filed: Oct. 13, 2015

(65) Prior Publication Data
US 2016/0106961 A1 Apr. 21, 2016

Related U.S. Application Data

(60) Provisional application No. 62/064,832, filed on Oct. 16, 2014.

(51) Int. Cl.
*A61M 25/10* (2013.01)
*A61L 29/14* (2006.01)
(Continued)

(52) U.S. Cl.
CPC ....... *A61M 25/1029* (2013.01); *A61L 29/041* (2013.01); *A61L 29/06* (2013.01);
(Continued)

(58) Field of Classification Search
CPC .......... A61M 25/1019; A61M 25/1002; A61M 2025/1031; A61M 25/1029; A61L 29/041;
(Continued)

(56) References Cited

U.S. PATENT DOCUMENTS 3,953,566 A * 4/1976 Gore ...................... B01D 71/36
264/505
5,587,125 A 12/1996 Roychowdhury
(Continued)

FOREIGN PATENT DOCUMENTS

EP 2644171 A1 10/2013
WO 96/04951 2/1996
(Continued)

OTHER PUBLICATIONS

International Search Report and Written Opinion for PCT/US2015/055469 dated Dec. 2, 2015, corresponding to U.S. Appl. No. 14/882,330, 5 pages.
(Continued)

*Primary Examiner* — Jenna Zhang

(57) ABSTRACT

The present disclosure is directed toward a composite balloon comprising a layer of material having a porous microstructure (e.g., ePTFE or expanded polyethylene) and a thermoplastic polymeric layer useful for medical applications. The layers of the composite balloons become adhered through a stretch blow-molding process. Methods of making and using such composite balloons are also described amongst others.

53 Claims, 13 Drawing Sheets

(51) Int. Cl.
*A61L 29/04* (2006.01)
*A61L 29/12* (2006.01)
*A61L 29/06* (2006.01)
*A61L 29/16* (2006.01)
*B29C 49/20* (2006.01)
*A61L 29/08* (2006.01)
*B29L 31/00* (2006.01)
*B29K 101/12* (2006.01)
*B29K 627/18* (2006.01)

(52) U.S. Cl.
CPC .......... *A61L 29/126* (2013.01); *A61L 29/146* (2013.01); *A61L 29/16* (2013.01); *A61M 25/1002* (2013.01); *B29C 49/20* (2013.01); *A61L 29/085* (2013.01); *A61M 2025/1031* (2013.01); *B29C 2049/2047* (2013.01); *B29K 2101/12* (2013.01); *B29K 2627/18* (2013.01); *B29L 2031/7543* (2013.01)

(58) Field of Classification Search
CPC ...... A61L 29/06; A61L 29/126; A61L 29/146; A61L 29/16; A61L 29/085; B29C 49/20; B29C 2049/2047; B29K 2101/12; B29K 2627/18; B29L 2031/7543
See application file for complete search history.

(56) References Cited

U.S. PATENT DOCUMENTS

| | | | |
|---|---|---|---|
| 5,708,044 A | 1/1998 | Branca | |
| 6,541,589 B1 | 4/2003 | Baillie | |
| 6,743,388 B2 | 6/2004 | Sridharan et al. | |
| 6,756,094 B1 | 6/2004 | Wang et al. | |
| 6,946,173 B2 | 9/2005 | Lim et al. | |
| 7,521,010 B2* | 4/2009 | Kennedy | B29C 55/005 264/113 |
| 7,531,611 B2 | 5/2009 | Sabol et al. | |
| 8,133,559 B2 | 3/2012 | Lee et al. | |
| 8,637,144 B2 | 1/2014 | Ford | |
| 8,937,105 B2 | 1/2015 | Xu et al. | |
| 2004/0197501 A1 | 10/2004 | Sridharan | |
| 2009/0076449 A1* | 3/2009 | Geis | A61M 25/0009 604/103.05 |
| 2010/0114019 A1* | 5/2010 | Dunn | A61F 2/954 604/101.01 |
| 2012/0064273 A1* | 3/2012 | Bacino | B01D 69/12 428/36.5 |
| 2012/0083733 A1* | 4/2012 | Chappa | A61M 25/10 604/103.02 |
| 2013/0030406 A1 | 1/2013 | Deshmukh et al. | |
| 2013/0226131 A1* | 8/2013 | Bacino | A61L 29/146 604/500 |
| 2013/0261547 A1 | 10/2013 | Aggerholm et al. | |
| 2013/0274660 A1 | 10/2013 | Aggerholm et al. | |
| 2014/0276585 A1 | 9/2014 | Gianotti | |
| 2015/0105723 A1 | 4/2015 | Fillmore et al. | |

FOREIGN PATENT DOCUMENTS

| | | |
|---|---|---|
| WO | WO-2012/122023 A2 | 9/2012 |
| WO | 2013/052572 | 4/2013 |

OTHER PUBLICATIONS

European Search Report from EP18165095.3, dated Jul. 4, 2018, 7 pages.

* cited by examiner

| Pattern | Time (S) | Temperature (F) | Pressure (Bar) |
|---|---|---|---|
| 111 | 20 | 350 | 15 |
| 112 | 20 | 350 | 25 |
| 113 | 20 | 350 | 35 |
| 121 | 20 | 285 | 15 |
| 122 | 20 | 285 | 25 |
| 123 | 20 | 285 | 35 |
| 131 | 20 | 325 | 15 |
| 132 | 20 | 325 | 25 |
| 133 | 20 | 325 | 35 |
| 211 | 45 | 350 | 15 |
| 212 | 45 | 350 | 25 |
| 213 | 45 | 350 | 35 |
| 221 | 45 | 285 | 15 |
| 222 | 45 | 285 | 25 |
| 223 | 45 | 285 | 35 |
| 231 | 45 | 325 | 15 |
| 232 | 45 | 325 | 25 |
| 233 | 45 | 325 | 35 |
| 311 | 70 | 350 | 15 |
| 312 | 70 | 350 | 25 |
| 313 | 70 | 350 | 35 |
| 321 | 70 | 285 | 15 |
| 322 | 70 | 285 | 25 |
| 323 | 70 | 285 | 35 |
| 331 | 70 | 325 | 15 |
| 332 | 70 | 325 | 25 |
| 333 | 70 | 325 | 35 |

FIG. 7a

| Film | Peak Kinetic Force (N) | | | | | | | | | | Mean |
|---|---|---|---|---|---|---|---|---|---|---|---|
| | Run 1 | | Run 2 | | Run 3 | | Run 4 | | Run 5 | | |
| | IMASS (N) | N/m | IMASS (N) | N/m | IMASS (N) | N/m | IMASS (N) | N/m | IMASS (N) | N/m | |
| Ex. 1 | 0.059 | 1.964 | 0.056 | 1.891 | 0.047 | 1.582 | 0.050 | 1.669 | 0.051 | 1.703 | 1.762 |
| Ex. 2 | 0.249 | 8.358 | 0.259 | 8.677 | 0.267 | 8.934 | 0.271 | 9.085 | 0.271 | 9.085 | 8.828 |

FIG. 7b(i)

| Film | Average Kinetic Force (N) | | | | | | | | | | Mean |
|---|---|---|---|---|---|---|---|---|---|---|---|
| | Run 1 | | Run 2 | | Run 3 | | Run 4 | | Run 5 | | |
| | IMASS (N) | N/m | IMASS (N) | N/m | IMASS (N) | N/m | IMASS (N) | N/m | IMASS (N) | N/m | |
| Ex. 1 | 0.027 | 0.765 | 0.040 | 1.341 | 0.044 | 1.475 | 0.046 | 1.531 | 0.042 | 1.173 | 1.257 |
| Ex. 2 | 0.219 | 6.124 | 0.234 | 7.844 | 0.239 | 8.001 | 0.239 | 8.018 | 0.245 | 8.208 | 7.639 |

BLOW MOLDED COMPOSITE DEVICES AND METHODS

FIELD OF THE INVENTION

The present disclosure generally relates to composite materials and methods of making the composite materials or medical device comprising the composite materials. The described composite materials can comprise a porous layer adhered to a blow moldable polymer, such as a composite material that comprises an expanded fluoropolymer layer that is adhered to a blow moldable polymer through a stretch blow molding process. In particular, the precursors for the composite material can be subject to a stretch blow molding process to form the composite material with a balloon shape for medical balloon catheter devices.

BACKGROUND

Medical balloons are useful for many endovascular treatments including dilatation of a body vessel, and drug delivery, and expansion and seating of a medical device such as a stent. Medical balloons may be made of a single layer of material or of multiple layers of material. In the case of multi-layer or composite balloons, the multiple layers within the composite may be different materials to obtain a blend of physical or chemical properties to optimize performance in some particular way(s), depending on the application.

Expanded polytetrafluoroethylene (ePTFE) is of interest for use in medical balloons because of its low coefficient of friction, chemical resistance, porous microstructure, flexibility, and strength. Because of the physical properties of ePTFE, however, the material cannot be processed in the same way that conventional thermoplastic elastomers are processed. In particular, adhering ePTFE to other materials is difficult because it has a low surface energy and a very high melt viscosity. New composite materials with ePTFE and ways of making said composites can be beneficial.

SUMMARY

The present disclosure is directed to composite balloons comprising a porous polymer layer such as ePTFE adhered to a blow moldable polymeric layer and a stretch-blow molding process to form such composite balloons.

In one aspect of the disclosure, a composite medical balloon is described. Some composite medical balloon embodiments can comprise a balloon wall defining a chamber and comprising a layered material, wherein the layered material comprises a polyamide layer at least partially adhered to a polymeric layer comprising a porous microstructure, wherein the porous polymeric layer is an outermost layer. Others can comprise a balloon wall defining a chamber and comprising a layered material, wherein the layered material comprises a seamless polymeric layer at least partially adhered to a polymeric layer comprising a porous microstructure, wherein the porous polymeric layer is an outermost layer and wherein the seamless polymeric layer is a compliant, semi-compliant, or non-compliant material. Still others can comprise a balloon wall defining a chamber and comprising a layered material, wherein the layered material comprises a first polymeric layer at least partially adhered to a second, anisotropic or isotropic polymeric layer comprising a porous microstructure. Other balloon embodiments can comprise a balloon wall defining a chamber and comprising a layered material, wherein the layered material comprises a seamless polymeric layer mechanically adhered to a seamless polymeric layer comprising a porous microstructure, wherein the porous polymeric layer is an outermost layer. In various embodiments, the porous polymeric layer is an expanded fluoropolymer, such as expanded polytetrafluoroethylene. The first or seamless polymeric layer is a blow moldable thermoplastic, such as polyamide. Depending on the selection of the material of the first or seamless polymeric layer, the balloon can be compliant, semi-compliant, or non-compliant. The underlying layer can be configured to prevent an inflation fluid from passing through the balloon wall.

In a further aspect of the disclosure, a medical balloon can comprise a balloon wall defining a chamber and comprising a layered material that defines an outer surface of the medical balloon, wherein the layered material comprises a polymeric layer having a porous microstructure and wherein the layered material comprises one or more recessed regions or one or more protruding regions on the outer surface. The recessed regions comprise a region of collapsed pores in the porous polymeric layer. In some embodiments, the recessed regions comprise a porous polymeric layer thickness that is 90% or less relative to the porous polymeric layer thickness of the non-recessed region. For example, a recessed region can comprise a thickness that is 10%, 15%, 20%, 25%, 30%, 35%, 40%, 45%, 50%, 55%, 60%, 65%, 70%, 75%, 80%, 85%, or 90% of the thickness of the non-recessed region. The combination of recesses and protrusions can form a striated pattern, oriented radially or longitudinally. While some patterns are described, it is to be understood that the pattern can be any selected pattern, whether regular or random. In some embodiments, the maximum width of the protrusions can be between 0.1 mm to 1 mm, such as 0.1 mm, 0.2 mm, 0.3 mm, 0.4 mm, 0.5 mm, 0.6 mm, 0.7 mm, 0.8 mm, 0.9 mm, 1.0 mm or any value therebetween. In various embodiments, the balloon surface defines a plurality of recesses and protrusions within the working length and wherein the protrusions cover about 30%, 35%, 40%, 45%, 50%, 55%, 60%, 65%, 70%, or any value therebetween of the total balloon surface area within the working length.

Other aspects of the disclosure are directed to methods of using the described composite balloons in a medical procedure. Such methods can comprise passing the balloon catheter device with a composite balloon mounted thereon through an anatomical conduit or vessel to the desired position and inflating the described balloon to a nominal diameter. The method can further comprise expanding a medical device that is disposed about the balloon or delivering, upon inflation, a therapeutic agent that is on the outer surface of the balloon to a surrounding tissue or endovascular device.

Still other aspects of the disclosure relate to methods of making the described balloon composites. Various embodiments comprise radially expanding, in a mold, a thermoplastic balloon preform and a polymeric tubular member comprising a porous microstructure to form a layered balloon body, wherein the tubular member is disposed about the balloon preform and wherein the portions of the tubular member and the balloon preform within the mold become mechanically adhered while in a radially expanded state. Some embodiments comprise radially expanding, in a mold, a thermoplastic balloon preform and a polymeric tubular member comprising a porous microstructure, wherein the tubular member is disposed about the balloon preform and applying heat to the radially expanded balloon preform and the polymeric tubular member at a temperature at or above the glass transition temperature of the thermoplastic balloon preform but below the melt temperature ($T_m$) of the thermoplastic balloon preform to form a layered balloon body. The portions of the outermost polymeric layer and the underlying layer within the mold become mechanically adhered while in a radially expanded state.

In an alternative embodiment, the balloon body may be formed in full from a balloon preform without first adding a polymeric tubular member comprising a porous microstructure. Some embodiments comprise radially expanding, in a mold, a thermoplastic balloon preform, and applying heat to the radially expanded balloon preform at a temperature at or above the glass transition temperature of the thermoplastic balloon preform but below the melt temperature ($T_m$) of the thermoplastic balloon preform to form a layered balloon body. The formed balloon body may be subjected to manual or mechanical pleating, folding, and other subsequent manual or mechanical manipulation prior to the addition of a polymeric tubular member comprising a porous microstructure. Once the polymeric tubular member comprising a porous microstructure is placed around a thermoplastic balloon body, a layered balloon body is formed. While the tubular member and balloon body are inflated within a mold, the temperature of the mold can be at or above the glass transition temperature ($T_g$) of the thermoplastic balloon body. For example, in various embodiments, the temperature can be between $T_g$ and $T_g+\frac{1}{2}(T_m-T_g)$; between $T_g$ and $T_g+\frac{1}{3}(T_m-T_g)$; or between $T_g$ and $T_g+\frac{1}{4}(T_m-T_g)$. ($T_m$ is the melt temperature of the thermoplastic balloon body.) In some embodiments, the temperature of the mold can be at or above the glass transition temperature ($T_g$) but below the melt temperature of the thermoplastic. In other embodiments, the temperature of the mold can be at or above the melt temperature of the thermoplastic. In this manner, the composite structure is formed into a composite balloon. The portions of the outermost polymeric layer and the underlying layer within the mold become mechanically adhered while in a radially expanded state in the formation of a composite balloon.

In some embodiments, the mold can have an inner surface that defines one or more recesses and wherein the formed composite balloon body comprises one or more recessed regions on the outer surface formed by a section of the tubular member being forced against a non-recessed section of the inner surface of the mold while in a radially expanded state. During radial expansion and heat setting, the temperature of the mold or inside the mold can be at or above the glass transition temperature ($T_g$) of the thermoplastic polymer. In further embodiments, the temperature is between the $T_g$ and the $T_m$ of the thermoplastic polymer. During radial expansion and heat setting, the pressure in the mold causing radial expansion (such as with an inflation fluid) can be between 15 bar to 40 bar for a mold of 4 to 8 mm in diameter. The pressure can depend on the compliancy of the selected blow moldable, thermoplastic polymer. The polymeric tubular member is a circumferentially or helically wrapped tube of a polymeric film.

Another aspect of the disclosure relates to methods of making the described composite balloons with one or more recesses and/or protrusions on the outer surface. In some embodiments, the method can comprise providing a mold having an inner surface that defines one or more recesses; radially expanding a polymeric tubular member comprising a porous microstructure in the mold to form a balloon body, wherein the balloon body comprises one or more recessed regions formed by a section of the tubular member being forced against a non-recessed section of the inner surface of the mold during expansion. The maximum width of the one or more recesses in the mold is between 0.1 mm to 1 mm, such as 0.1 mm, 0.2 mm, 0.3 mm, 0.4 mm, 0.5 mm, 0.6 mm, 0.7 mm, 0.8 mm, 0.9 mm, 1.0 mm or any value therebetween. The depth of each of the one or more mold recesses can be about 1.0x, 1.3x, 1.5x, 1.7x, or 2.0x, where x is the width of the recess. During radial expansion and heat setting, the temperature of the mold or inside the mold can be at or above the glass transition temperature ($T_g$) of the thermoplastic polymer. In further embodiments, the temperature is between the $T_g$ and the $T_m$ of the thermoplastic polymer. In still further embodiments, the temperature of the mold or in the mold can be at or above the melt temperature of the thermoplastic. During radial expansion and heat setting, the pressure in the mold causing radial expansion (such as with an inflation fluid) can be from 1 bar up to 40 bar for a mold of 4 to 8 mm in diameter. The pressure can depend on the compliancy of the selected blow moldable, thermoplastic polymer. The polymeric tubular member is a circumferentially or helically wrapped tube of a polymeric film.

Another aspect of the disclosure is a method of applying a therapeutic agent to the described balloons. In some embodiments, the method comprises applying one or more therapeutic agents to the balloon prior to mounting on a catheter. In further embodiments, the therapeutic agent is applied to the recesses on the balloon surface. In further embodiments, the therapeutic agent is applied to protrusions on the balloon surface. In still further embodiments, the therapeutic agent is applied to recesses and protrusions on the balloon surface.

Yet another aspect of the disclosure can be an assembly for making a medical balloon comprising a balloon mold defining a chamber; a thermoplastic balloon preform or fully formed balloon body; and a polymeric tubular member comprising a porous microstructure, wherein the tubular member is disposed about the balloon preform or the formed balloon body and wherein at least a portion of the tubular member and the balloon preform or the formed balloon body are disposed within the chamber.

The terms "a" and "an" are defined as one or more unless this disclosure explicitly requires otherwise.

The terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. The term "majorly" indicates at least half.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, any of the present devices, systems, and methods that "comprises," "has," "includes" or "contains" one or more elements possesses those one or more elements, but is not limited to possessing only those one or more elements. Likewise, an element of a device, system, or method that "comprises," "has," "includes" or "contains" one or more features possesses those one or more features, but is not limited to possessing only those one or more features.

Any of the present devices, systems, and methods can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Furthermore, a structure that is capable of performing a function or that is configured in a certain way is capable or configured in at least that way, but may also be capable or configured in ways that are not listed.

The preposition "between," when used to define a range of values (e.g., between x and y) means that the range includes the end points (e.g., x and y) of the given range and the values between the end points.

As used herein, "nominal diameter" means the approximate diameter of the balloon at the nominal inflation pressure. Beyond this state, pressure increases (e.g., up to the rated burst pressure) result in less than a 20% increase in diameter, less than a 15% increase in diameter, or less than a 10% increase in diameter. Typically, the nominal diameter is the labeled diameter as indicated on the instructions for the end user, e.g., a clinician.

The term "imbibed" or "imbibing" as used herein is meant to describe any state or mode for majorly or substantially filling a region of pores of a porous material such as ePTFE or the like but does not refer to filling the pores with a therapeutic agent or a therapeutic agent combined with excipients.

As used herein, "angioplasty pressure" means the minimum pressure required to perform a Percutaneous Transluminal Angioplasty (PTA) procedure for a balloon of a certain size. This value is dependent on the size of the balloon, and can be within the working pressure range between the nominal inflation pressure to the rated burst pressure, the nominal inflation pressure being the minimum pressure at which the balloon reaches nominal diameter and rated burst pressure being the upper limit of a pressure range for a medical balloon provided by the manufacturer.

As used herein, "balance ratio" means ratio of machine direction matrix tensile strength to transverse direction matrix tensile strength. Where the matrix tensile strengths in the machine and transverse direction are not substantially equal, a material can be said to be "anisotropic." Where the matrix tensile strength in the machine and transverse direction are substantially equal, the material can be said to be "isotropic".

As used herein, a "semi-compliant" balloon is one that has less than about 20% diametric growth (e.g., less than a 20% increase in the balloon diameter relative to the nominal diameter) when inflated from the nominal inflation pressure to the rated burst pressure. As used herein, a "non-compliant" balloon is one that has less than about 10% diametric growth when inflated from the nominal inflation pressure to the rated burst pressure. As used herein, a compliant balloon is one that has greater than 20% increase in the balloon diameter relative to the nominal diameter. Such a compliant balloon will conform to the shape of a vessel lumen.

As used herein, "medical device" means any medical device capable of being implanted and/or deployed within a body lumen or cavity. In various embodiments, a medical device can comprise an endovascular medical device such as a stent, a stent-graft, graft, heart valve, heart valve frame or pre-stent, occluder, sensor, marker, closure device, filter, embolic protection device, anchor, drug delivery device, cardiac or neurostimulation lead, gastrointestinal sleeves, and the like.

The feature or features of one embodiment may be applied to other embodiments, even though not described or illustrated, unless expressly prohibited by this disclosure or the nature of the embodiments.

Details associated with the embodiments described above and others are presented below.

BRIEF DESCRIPTION OF THE DRAWINGS

The features and advantages of the present disclosure will become more apparent from the detailed description set forth below when taken in conjunction with the drawings, wherein:

FIG. 1b illustrates a cross-section of the composite material forming the medical balloon embodiment shown in FIG. 1a.

FIG. 4 is a transverse, cross-sectional schematic of the interior surface of a balloon mold for forming a series of protrusions and recesses that create a striped pattern much like that depicted in FIG. 3a.

FIG. 7a is a table of the heat-setting conditions for the balloon bodies made in Example 3.

FIGS. 7b(i)-(ii) are tables of the results for the Peel Test described in Example 6.

DETAILED DESCRIPTION OF THE ILLUSTRATED EMBODIMENTS

Figure 1A:
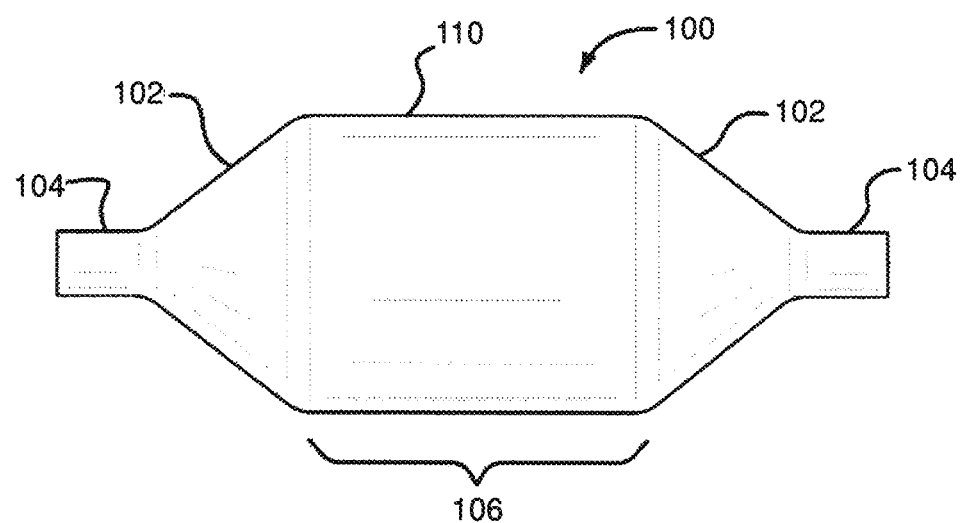
FIG. 1a illustrates a medical balloon embodiment in accordance with the present disclosure.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

Surprisingly, the inventors discovered that by stretch blow molding a thermoplastic polymeric preform with a porous tubular member (e.g., an ePTFE tube) surrounding it, the two separate members become adhered to form a composite balloon member without any adhesive agents or surface treatments. Similarly, a fully formed balloon body with a porous tubular member (e.g., an ePTFE tube) surrounding it can be heated and pressurized to form a composite balloon member without the use of any adhesive agents or surface treatments. Such blow molded composites can form a medical balloon that exhibits a lubricious outer surface, a low diametric profile, and/or rated burst pressures in the range of, e.g., 5 bar to 40 bar or more—the value being dependent upon the dimensions of the balloon and the properties of the respective layers amongst other things, and the orientation of the microstructure. The rated burst pressure and the compliance can be tailored based upon the material properties of the respective layers.

With such blow molded composite balloons, the outer layer material acts in a unitary manner with the underlying layer. In comparison, a discrete cover over a balloon can move independently of the underlying balloon causing the cover to gather or deform in certain areas, which can be unpredictable and/or undesired.

Another realized benefit relative to balloons with "floating" ePTFE covers involves the issue of trapped air. It is not uncommon for air to become trapped between the cover and the balloon of such devices, and a processing step to remove such trapped air between may be required to ensure patient safety. Composite balloons of the present disclosure would not have this issue as the layers are unitary without the use of a separate adhesive material or additional surface treatment step.

Accordingly, the present disclosure is directed towards a composite balloon comprising a layer of material having a porous microstructure (e.g., ePTFE or expanded polyethylene) and a thermoplastic polymeric layer useful for medical applications. As mentioned above, the layers of the composite balloons become adhered through a stretch blow molding process. The process conditions involve a temperature that is at or above the glass transition temperature ($T_g$) of the thermoplastic polymer. While not wishing to be bound by any particular theory, it is believed that the layers within the composite balloons of the present disclosure become mechanically adhered through the stretch blow molding process.

During the stretch blow molding process, due to the multi-directional pressures on the porous microstructure, some types of porous microstructure may collapse (and lose some loft), which may be undesired for some applications. Thus, to mitigate this effect, a patterned mold can be utilized that reduces this effect for a portion of the balloon's surface area. Accordingly, the present disclosure is also directed towards a composite balloon comprising an outermost layer of material having a porous microstructure and thermoplastic layer where the outer surface of the balloon comprises a recess (or protrusion) or a plurality of recesses (or protrusions). The recesses can be selectively formed by using a mold having a relief (or sunken relief) on its inner surface to create areas of more compression of the porous microstructure relative to protruding areas.

Figure 1B:
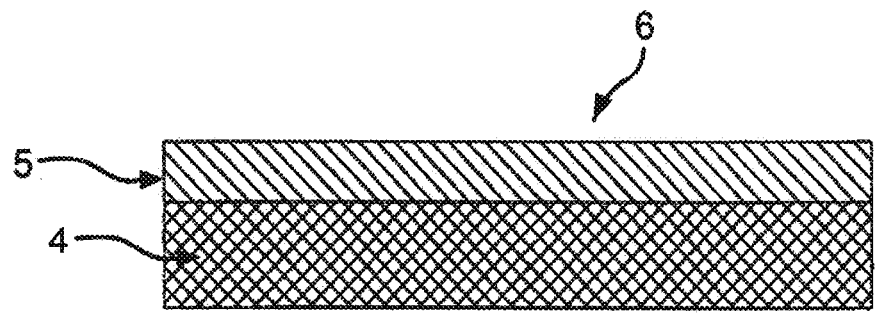

According to the present disclosure, with reference to FIGS. 1a-1b, a medical balloon 100 comprises a balloon wall 110 defining a chamber and comprising a layered material 6, wherein layered material 6 comprises a thermoplastic polymeric layer 4 at least partially adhered to a polymeric layer 5 comprising a porous microstructure (referred to herein as a "porous layer"). As mentioned above, the adhesion is created through a stretch blow molding process. In various embodiments, thermoplastic layer 4 serves as the bladder to retain the inflation fluid and thus is composed of an impermeable or fluid-tight material. In addition, in various embodiments, the porous polymeric layer 5 can be the innermost or outermost layer.

Figure 2:
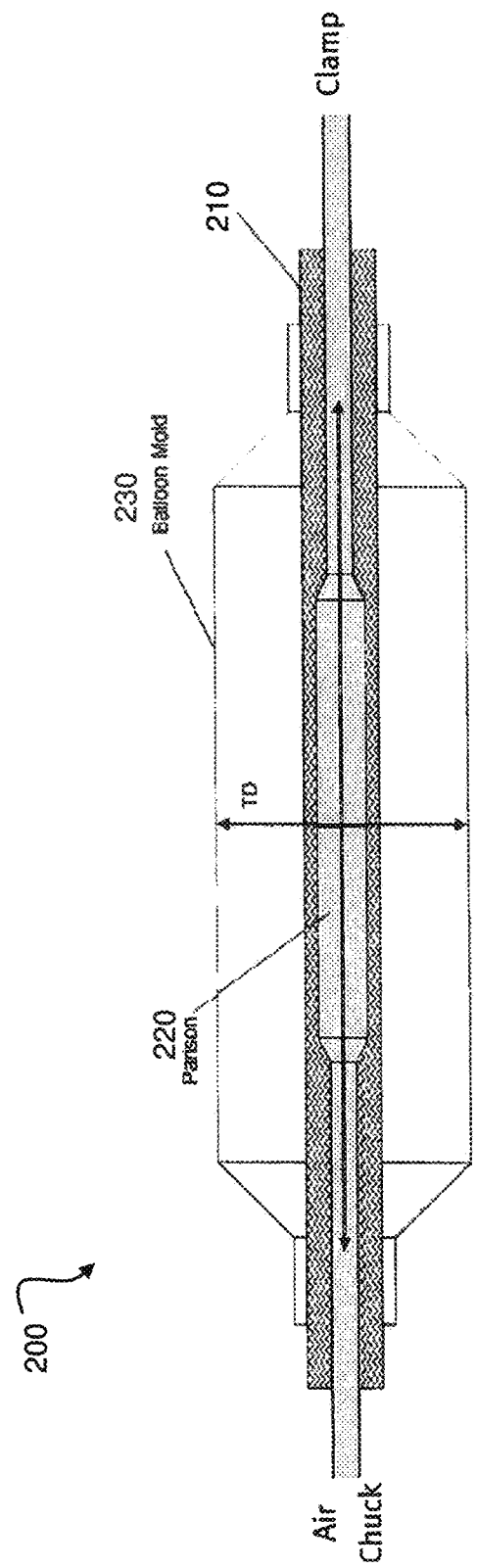
FIG. 2 is a schematic of a balloon mold with a tubular precursor positioned about a thermoplastic preform and disposed within the cavity of the mold.

In order to make such balloon body composites by one of the several methods described, with reference to FIG. 2, a polymeric tubular member 210 comprising a porous microstructure is placed around a thermoplastic balloon preform (parison) 220 and both are radially expanded in a balloon mold 230 to form a layered balloon body. While tubular member 210 and balloon preform (parison) 220 are inflated within balloon mold 230, the temperature of the mold can be at or above the glass transition temperature ($T_g$) of the thermoplastic balloon preform. For example, in various embodiments, the temperature can be between $T_g$ and $T_g+\frac{1}{2}(T_m-T_g)$; between $T_g$ and $T_g+\frac{1}{3}(T_m-T_g)$; or between $T_g$ and $T_g+\frac{1}{4}(T_m-T_g)$. ($T_m$ is the melt temperature of the thermoplastic preform.) In some embodiments, the temperature of the mold can be at or above the glass transition temperature ($T_g$) but below the melt temperature of the thermoplastic. In other embodiments, the temperature of the mold can be above the melt temperature of the thermoplastic.

In an alternative embodiment, the balloon body 100 is formed in full without first adding a polymeric tubular member comprising a porous microstructure. The formed balloon body 100 is subjected to manual or mechanical pleating, folding, and other subsequent manual or mechanical manipulation prior to the addition of a polymeric tubular member comprising a porous microstructure 210. The polymeric tubular member comprising a porous microstructure 210 is placed around a thermoplastic balloon body 310. When tubular member 210 and balloon body 100 are inflated within mold 230, the temperature of the mold is raised to or above the glass transition temperature ($T_g$) of the thermoplastic balloon preform. For example, in various embodiments, the temperature is between $T_g$ and $T_g+\frac{1}{2}(T_m-T_g)$; between $T_g$ and $T_g+\frac{1}{3}(T_m-T_g)$; or between $T_g$ and $T_g+\frac{1}{4}(T_m-T_g)$. ($T_m$ is the melt temperature of the thermoplastic preform.) In some embodiments, the temperature of the mold is at or above the glass transition temperature ($T_g$) but below the melt temperature of the thermoplastic. In other embodiments, the temperature of the mold is above the melt temperature of the thermoplastic. In this manner, the composite structure is formed into a composite balloon.

Through this process, the portions of tubular member 210 and underlying thermoplastic preform (parison) 220 within balloon mold 230 become at least partially adhered. The adhesion created through this process is referred to herein as "mechanical adhesion." The mechanical adhesion is not caused by an adhesive agent (e.g., a glue) or by chemical bonds (covalent or ionic bonds). While not wishing to be bound by any particular theory, it is postulated that the mechanical adhesion observed in the embodiments described herein is caused by a conforming or interlocking of a polymer with the surface irregularities (e.g., a porous microstructure) of the porous polymer. This process results in adhering the two layers 4, 5 (FIG. 1b.) together.

In various embodiments, the degree of adhesion can be increased by increasing the temperature during the shape-setting phase of the blow molding process, which occurs in the later portion of the process. In addition, the degree of adhesion can be increased by increasing the pressure during the shape-setting phase of the blow molding process. The pressure during the shape-setting phase can be up to 40 bar depending on the materials being used and the intended results of the process. In various embodiments, the pressure during the shape-setting phase can be 5 bar, 10 bar, 15 bar, 20 bar, 25 bar, 30 bar, 40 bar, 45 bar, 50 bar, 60 bar, or any value therebetween. While a pressure range has been indicated, it is to be understood that pressures can exceed the high end of the stated range because the mold will provide a counter force that prevents the forming balloon from deforming or bursting. It is also to be understood that pressures may be lower than those stated, as the pressure needed to cause radial expansion will depend on the strength and thickness of the materials (balloon preforms or balloon bodies and tubular members) used. Because of the manner in which the balloon body is formed, the thermoplastic polymer preform 220 and ultimately the layer in the composite balloon wall can be seamless.

In accordance with another aspect of the disclosure, a balloon molding assembly 200, as shown in FIG. 2, can comprise polymeric tubular member 210 comprising a porous microstructure disposed around a thermoplastic balloon preform (parison) 220 and positioned within the chamber of balloon mold 230.

Preform (parison) 220 can be formed in any variety of polymeric processes, e.g. an injection molding, a blow molding, or an extrusion process. In some embodiments, preform (parison) 220 can be pre-conditioned by stretching in a balloon stretch machine under elevated temperatures before the composite-forming step in order to increase the reliability of the composite-forming step. In various embodiments, preform (parison) 220 is stretched at least 1.5x, 2x, 2.5x, or 3x its length.

The thermoplastic layer 4 or preform (parison) 220 can be composed of a compliant, semi-compliant or non-compliant thermoplastic polymer. Suitable thermoplastics include polymers that are medical grade and are blow moldable. In various embodiments, the thermoplastic material can have a glass transition temperature below 360° C., 325° C., 300° C., 275° C., 250° C., 225° C., 200° C. or any value therebetween. Examples of suitable thermoplastics can include polymethyl methacrylate (PMMA or Acrylic), polystyrene (PS), acrylonitrile butadiene styrene (ABS), polyvinyl chloride (PVC), modified polyethylene terephthalate glycol (PETG), cellulose acetate butyrate (CAB); semi-crystalline commodity plastics that include polyethylene (PE), high density polyethylene (HDPE), low density polyethylene (LDPE or LLDPE), polypropylene (PP), polymethylpentene (PMP); polycarbonate (PC), polyphenylene oxide (PPO), modified polyphenylene oxide (Mod PPO), polyphenylene ether (PPE), modified polyphenylene ether (Mod PPE), thermoplastic polyurethane (TPU); polyoxymethylene (POM or Acetal), polyethylene terephthalate (PET, Thermoplastic Polyester), polybutylene terephthalate (PBT, Thermoplastic Polyester), polyimide (PI, Imidized Plastic), polyamide-imide (PAI, Imidized Plastic), polybenzimidazole (PBI, Imidized Plastic); polysulfone (PSU), polyetherimide (PEI), polyether sulfone (PES), polyaryl sulfone (PAS); polyphenylene sulfide (PPS), polyether ether ketone (PEEK); fluoropolymers that include fluorinated ethylene propylene (FEP), ethylene chlorotrifluoroethylene (ECTFE), ethylene tetrafluoroethylene (ETFE), polychlorotrifluoroethylene (PCTFE), polyvinylidene fluoride (PVDF), perfluoroalkoxy (PFA), or combinations, copolymers, or derivatives thereof. Other commonly known medical grade materials include elastomeric organosilicon polymers, and polyether block amide (e.g., PEBAX®). In particular, polyamides can include nylon 12, nylon 11, nylon 9, nylon 6/9, and nylon 6/6. In certain embodiments, PET, nylon, and PE may be selected for medical balloons used in coronary angioplasty or other high pressure applications. The specific choice of materials depends on the desired characteristics/intended application of the balloon.

As described above, the porous layer is formed from tubular member 210 of a polymer having a porous microstructure. Tubular member 210 can be formed as an extruded tube or can be film-wrapped. Tubular member 210 can have circumferential, helical, or axial orientations of the microstructure. In various embodiments, tubular member 210 can be formed by wrapping a film or tape and the orientation can be controlled by the angle of the wrapping. Tubular member 210 can be circumferentially wrapped or helically wrapped. When the porous material is wrapped helically versus circumferentially or axially, the degree of compliancy in a given direction can be varied and can influence the overall compliancy of the composite. (As used herein, the term "axial" is interchangeable with the term "longitudinal." As used herein, "circumferential" means an angle that is substantially perpendicular to the longitudinal axis.)

The porous tubular member 210 can be isotropic or anisotropic. In various embodiments, in the composite material, the anisotropic porous polymeric layer is oriented such that the balloon wall has a higher tensile strength in the longitudinal direction than the radial direction. In other embodiments, the anisotropic porous polymeric layer is oriented such that the balloon wall has a lower tensile strength in the longitudinal direction than the radial direction. In various embodiments, the balance ratio of the material layer can be between 1:1 and 70:1, such as 2:1, 5:1, 7:1, 10:1, 12:1, 14:1, 16:1, 18:1, 20:1, 22:1, 24:1, 26:1, 28:1, 30:1, 35:1, 40:1, 45:1, 50:1, 55:1, 60:1, 65:1, 70:1, or any value or range therebetween. In embodiments where the thermoplastic polymer is a compliant material, the axial modulus and/or longitudinal modulus, and thus the balance ratio can be tuned to control distension in the radial and/or longitudinal direction.

The architecture of porous microstructure can be selected based on the needs of the intended application. In various embodiments, the porous microstructure can be substantially fibrillated (e.g., a non-woven web having a microstructure of substantially only fibrils, some fused at crossover points or with smaller nodal dimensions). In other embodiments, the porous material can comprise large nodes or large densified regions that may have an impact on the extent of compressibility/collapsibility of the material during blow molding. In still other embodiments, the porous microstructure can be a node and fibril microstructure between these two. In some embodiments, the porous material can have an "open" microstructure such that the outer layer can have more loft and/or a drug coating can have more void space to occupy near the surface of the layer. The material described in Example 1 is an example of a material that comprises an open microstructure. Other examples of porous architectures can be fibrous structures (such as woven or braided fabrics), non-woven mats of fibers, microfibers, or nanofibers, flash spun films, electrospun films, and other porous films.

In various embodiments, the porous material can comprise expanded fluoropolymers or expanded polyethylene (see e.g., U.S. Pat. No. 6,743,388 to Sridharan (et al.). Non-limiting examples of expandable fluoropolymers include, but are not limited to, ePTFE, expanded modified PTFE, and expanded copolymers of PTFE. Patents have been filed on expandable blends of PTFE, expandable modified PTFE, and expanded copolymers of PTFE, such as, for example, U.S. Pat. No. 5,708,044 to Branca; U.S. Pat. No. 6,541,589 to Baillie; U.S. Pat. No. 7,531,611 to Sabol et al.; U.S. Pat. No. 8,637,144 to Ford; and U.S. Pat. No. 8,937,105 to Xu et al.

In various embodiments, the pores of a portion of the porous layer can be devoid of a polymeric filler material, except for perhaps the interface between the two layers. In this way, the porous material can comprise microstructure that is not imbibed with a second polymeric material. While some embodiments of the present disclosure are not imbibed, it is to be understood that by increasing the temperature and/or pressure, deeper penetration into the porous material can be caused.

The degree of adhesion between the layers is measurable by a "Peel Test" as described herein. In various embodiments, the two layers of the composite are capable of separating in a 157° Peel Test with a minimum of 1 N/m of average kinetic force. In various embodiments, the average kinetic force of the Peel Test can be at least 5 N/m, 10 N/m, 15 N/m, 20 N/m, 25 N/m, 30 N/m, 35 N/m, 40 N/m or between any range derivable therefrom. This range can be further expanded up to the tensile limit of either layer of composite material, and is dependent upon the nature of the materials used. The amount of adhesion can be increased by increasing the temperature and/or pressure of the blow molding process.

In various embodiments, the rated burst pressure of a balloon can be higher than what the balloon would otherwise be without the incorporation of the porous layer. For example, a composite balloon in accordance herewith and comprising an underlying polyurethane layer would have a higher rated burst pressure than a polyurethane balloon formed from the same precursor. In addition, for some non-compliant composite balloon embodiments in accordance herewith, the rated burst pressure can be 10 bar, 15 bar, 20 bar, 25 bar, 30 bar, 35 bar, 40 bar, 45 bar, 50 bar, 55 bar, 60 bar or more for a 4 to 8 mm in nominal diameter medical balloon.

Figure 3A:
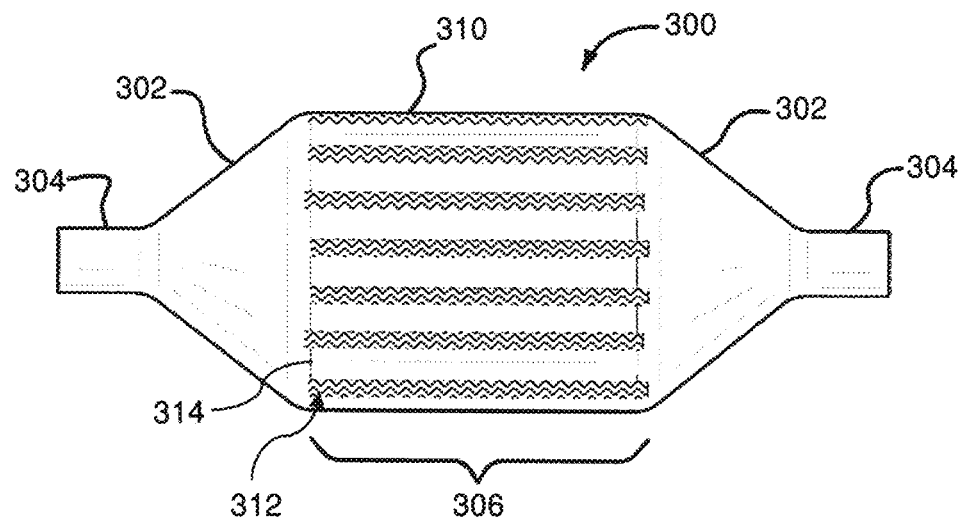
FIG. 3a illustrates a medical balloon embodiment comprising a relief pattern on the outer surface in accordance with the present disclosure.
Figure 3B:
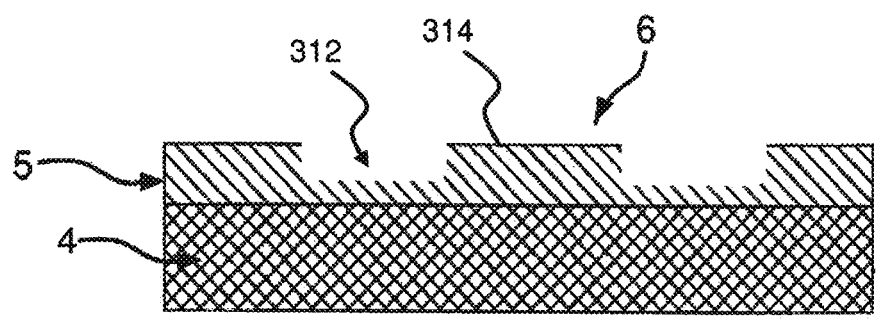
FIG. 3b illustrates a cross-section of the composite material forming the medical balloon embodiment shown in FIG. 3a and showing the recesses and protrusions in the outer surface.

In accordance with another aspect of the present disclosure, the composite balloon body can be formed in a patterned/relief mold to create an outer balloon surface with one or more recesses or protrusions. With reference to FIGS. 3a-3b, an embodiment of medical balloon 300 can comprise a balloon wall 310 defining a chamber and comprising a layered material 6, and the outer surface of balloon wall 310 can define one or more recesses 312 or protrusions 314. In particular, layered material 6 comprises polymeric layer 5 having a porous microstructure and defining at least one recessed region 312 and/or at least one protruding region 314. A "recessed" region 312 can be a region with a higher degree of collapsed pores in the porous polymeric layer. A "protruding" region 314 can be a region adjacent recess 312 and has a lower degree of collapsed pores, if any.

The depth of recess 312 (or at least the relative amount of compression between recessed region 312 and non-recessed (or protruding) region 314 can be measured by comparing the thicknesses between two adjacent regions 312, 314. In various embodiments, recessed region 312 has a porous polymeric layer thickness that is approximately 90% relative to the porous polymeric layer thickness of the non-recessed region 314. A slight recess 312 might be one that is between 80% to 90% relative thickness, whereas a deep recess can be between 10% to 30% relative thickness. The amount of compression can be to some extent selectively adjusted through a number of factors including the width of the patterned mold recess features, the width of the non-recessed features of the mold, the depth of the mold recess features, the pressure and temperature of the process, the ratio of protruding features to recessed features, the surface area density of mold recess features, the z-axis compressibility of the porous material, and the compliancy of the preform material. By controlling the process and selecting certain materials, in various embodiments, a recess's 312 relative thickness can be 10%, 20%, 25%, 30%, 40%, 50%, 55%, 60%, 65%, 70%, 75%, 80%, 85%, 90%, or any value therebetween compared to a non-recessed or protruding region. Because a protruding region 314 is protruding due to its proximity to recessed region 312, the degree of protrusion can be controlled by the same factors.

Figure 4:
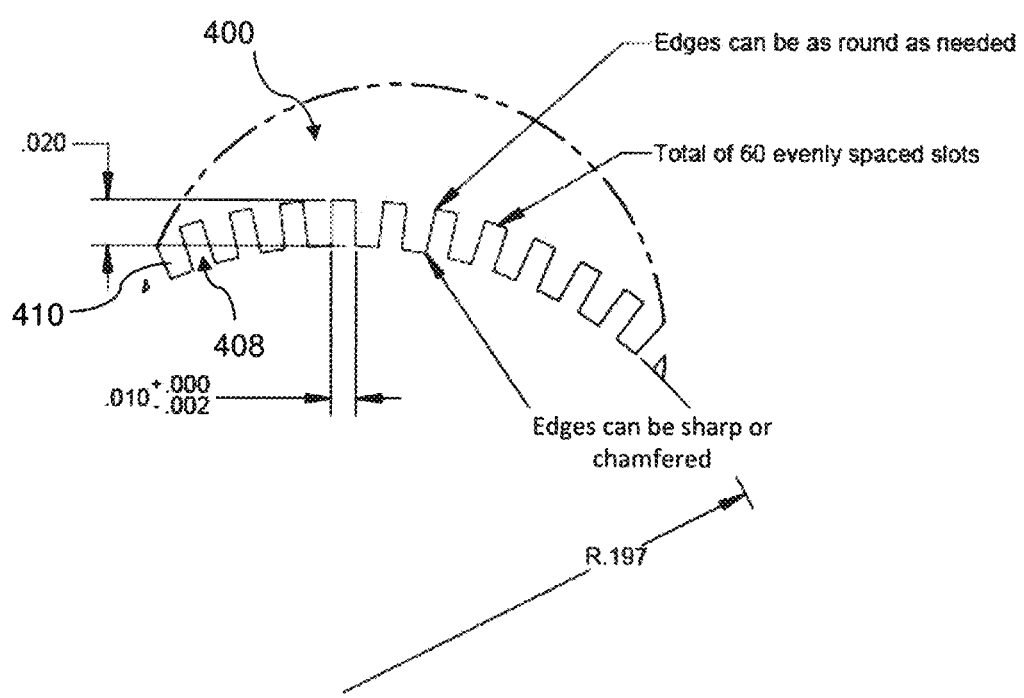

In addition to varying the degree of recess or degree of protrusion, the pattern of recesses 312 or protrusions 314 can also be varied by selectively varying the pattern of the mold. FIG. 4 illustrates a schematic transverse cross-sectional portion of a patterned balloon mold 400. Shown are the relief features of the inner surface which comprise a recess 408 and a protrusion 410. A recess pattern on the mold can be any random or repeated pattern. In various embodiments, the pattern is a longitudinal or circumferential striped/striated pattern, a helical pattern, a polka dot pattern, a sinusoidal or zig-zag pattern, or any combination thereof. The pattern can be dictated by the application or can impart some benefit to the application. For example, in some embodiments, the outer surface of the balloon can have a plurality of longitudinal striations or grooves and the grooves may facilitate pleating and folding the balloon into a delivery configuration and/or re-pleating the balloon after deflation. In addition, in various embodiments, the recess features within the mold can have chamfered or rounded corners to reduce the strain on the porous layer at these recess/protrusion transition areas during formation.

Mold recess 408 will facilitate the formation of a protruding feature 314 on the balloon by being appropriately sized in both width to allow the porous polymer to extend into recess 408 and tailoring the extent of which the underlying thermoplastic polymer extends into the recess. Moreover, the depth of recess 408 can be tailored to vary the height or degree of compression of a protrusion. Through consideration and selection of a width and depth of a mold recess, a temperature and pressure of the blow molding process, and the balloon preform compliancy, this result can be achieved and even tuned to obtain a desired relative thickness and degree of microstructure compression.

A region of balloon 300 with a higher surface area of recesses 312 than protrusions 314 will have lower compliance than a region with a higher surface area of protrusions 314 than recesses 312. Thus, tailoring the ratio of recesses 312 and protrusions 314 by region on the balloon body can be a way to tune the inflation profile of the balloon. For example, if it is desired to have the end portions of balloon 300 reach nominal diameter faster than the center, the end portions of balloon 300 can be a higher proportion of protrusions 314 to recesses 312 than the central portion of balloon 300.

The pattern of the mold can be selectively varied to define the percentage of the total balloon surface area that is a protruding region, or conversely, a recessed region. In some embodiments, the plurality of the protrusion can cover 1% to 90% of the total balloon surface area. In particular embodiments, the percentage of surface area that has a surface protrusion can be 1%, 10%, 20%, 30%, 40%, 50%, 60%, 70%, 80%, 90%, 99% or any value or range therebetween.

The described medical balloons like the embodiments depicted in FIGS. 1 and 3 can have any appropriate dimension and sized for the clinical application. Typically, a medical balloon is generally cylindrical along the working length. As shown, balloon 100, 300 have two opposed leg portions 104, 304 that are integrally connected to shoulder/tapered portions 106, 306. For the purposes of this disclosure, "working length" is defined as the length of the straight body section 106, 306 of a balloon 110, 310 which comprises the approximate length between the opposed shoulder/tapered portions 106, 306. Leg portions 104, 304, shoulder/tapered portions 106, 306 and straight body section 108, 308 defines a balloon overall length. The working length of balloon 100, 300 can be about 10 mm to about 150 mm or more. Similarly, the nominal diameter of the balloon can be about 2 mm to about 30 mm or more. By way of example, a balloon can have a 4 mm diameter and a 30 mm working length, or alternatively, an 8 mm diameter and about a 60 mm working length. Of course, the balloon of the present disclosure can be constructed at any dimensions appropriate for the specific use.

Porous polymeric layer 5 can extend over the entirety of balloon 100, 300 or only be located on a portion of the balloon 100, 300. For example, porous polymeric layer 5 can extend only on body 108, 308 of balloon 100, 300 or can only be located over one or more shoulder/tapered portions 106, 306. During the making of balloon 100, 300, tubular polymer member 210 comprising a porous microstructure can be appropriately sized and positioned to the desired location over thermoplastic preform (parison) 220 in order to tailor where porous polymeric layer 5 is located on balloon 100, 300.

Figure 5A:
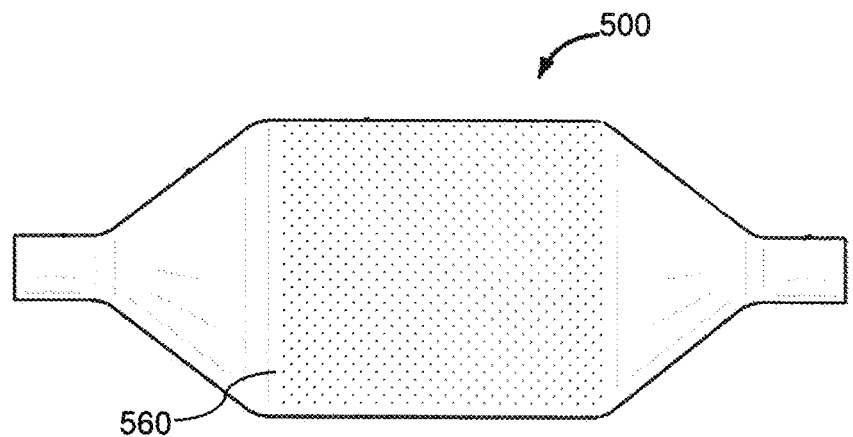
FIG. 5a illustrates a medical balloon embodiment in accordance with the present disclosure with a coating of a therapeutic agent.

By way of example, with reference to FIG. 5a, the balloon 500 in accordance with the present disclosure can be coated with a therapeutic agent 560. In further embodiments, a retractable sheath (not shown) can be located about the balloon 500 to prevent or minimize release of said therapeutic agent 560 until the balloon 500 is at the desired treatment site. In various embodiments, an open porous microstructure can facilitate therapeutic agent loading, the retention of the therapeutic agent on the balloon during processing, and delivery of the therapeutic agent. Similarly, in a "patterned" balloon embodiment, the size and pattern of the recesses can also influence the amount of loading, the retention of therapeutic agent on the balloon during processing, and the delivery of the therapeutic agent to the surrounding tissue upon inflation. In order to facilitate coating and adhesion of a therapeutic agent, the surface of the porous layer can be plasma treated.

A "therapeutic agent," as used herein, is an agent that can induce a bioactive response or be detectable by an analytical device. Such agents include, but are not limited to, radiopaque compounds, cilostazol, everolimus, dicumarol, zotarolimus, carvedilol, anti-thrombotic agents such as heparin, heparin derivatives, urokinase, and dextrophenyl-alanine proline arginine chloromethylketone; anti-inflammatory agents such as dexamethasone, prednisolone, corticosterone, budesonide, estrogen, sulfasalazine and mesalamine, sirolimus and everolimus (and related analogs), anti-neoplastic/anti-proliferative/anti-mitotic agents such as major taxane domain-binding drugs, such as paclitaxel and derivatives or analogues thereof, epothilone, discodermolide, docetaxel, protein-bound paclitaxel particles such as ABRAXANE® (ABRAXANE is a registered trademark of ABRAXIS BIOSCIENCE, LLC), paclitaxel complexed with an appropriate cyclodextrin (or cyclodextrin-like molecule or other clathrate), rapamycin and derivatives or analogues thereof, rapamycin (or rapamycin analogs) complexed with an appropriate cyclodextrin (or cyclodextrin-like molecule or other clathrate); 17β-estradiol, 17β-estradiol complexed with an appropriate cyclodextrin or other clathrate; dicumarol, dicumarol complexed with an appropriate cyclodextrin or other clathrate; β-lapachone and analogues thereof, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; an RGD peptide-containing compound, AZX100 (a cell peptide that mimics HSP20; Capstone Therapeutics Corp., USA), hirudin, anti-thrombin compounds, platelet receptor antagonists, anti-thrombin antibodies, antiplatelet receptor antibodies, aspirin, prostaglandin inhibitors, platelet inhibitors and tick antiplatelet peptides; vascular cell growth promoters such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bi-functional molecules consisting of a growth factor and a cytotoxin, bi-functional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; agents that interfere with endogenous vasoactive mechanisms; inhibitors of leukocyte recruitment, such as monoclonal antibodies; cytokines; hormones or a combination thereof. In one embodiment, said therapeutic agent is a hydrophilic agent. In another embodiment, said therapeutic agent is a hydrophobic agent. In another embodiment, said therapeutic agent is paclitaxel.

In various embodiments, the coating on the balloon can comprise a therapeutic agent such as paclitaxel and at least one excipient. Such excipients can be a non-polymeric organic additive. For example, the (at least one) organic additive can be independently selected from a list consisting of 4-aminobenzoic acid, saccharin, ascorbic acid, methyl paraben, caffeine, calcium salicylate, pentetic acid, creatinine, ethylurea, acetaminophen, aspirin, theobromine, tryptophan, succinic acid, glutaric acid, adipic acid, theophylline, and saccharin sodium. More particularly, the (at least one) organic additive can be independently selected from the list consisting of 4-aminobenzoic acid, methyl paraben, caffeine, calcium salicylate and succinic acid. In one embodiment the organic additive is succinic acid. In another embodiment, the organic additive is caffeine.

Figure 5B:
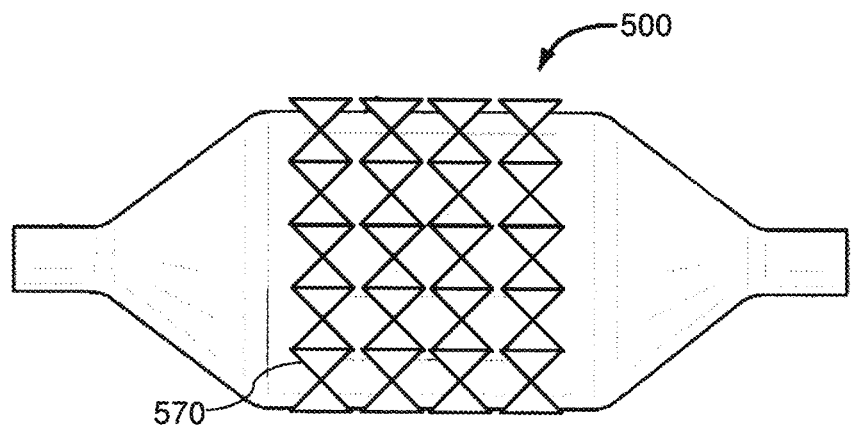
FIG. 5b illustrates a medical balloon embodiment in accordance with the present disclosure with a stent device disposed thereon.

By way of second example, with reference to FIG. 5b, balloon 500 in accordance with the present disclosure can comprise medical device 570 disposed about balloon 500. Balloon 500 can be used to expand medical device 570 or touch up a medical device previously deployed or implanted. As shown, medical device 570 is a stent, and more particularly a segmented stent, e.g., a stent comprising a plurality of discrete annular stent members. As previously mentioned, the stent can be balloon expandable or self-expanding.

A method of making a medical balloon in accordance with the present disclosure can comprise wrapping a film about a mandrel circumferentially or helically to form a tubular precursor. The wrapped film can be bonded, such as through a heat treatment, and then removed as a tubular precursor from said mandrel. The tubular precursor can then be placed around a balloon preform (parison) and placed into a mold to undergo a stretch blow molding process. In an alternative embodiment, the tubular precursor can be placed around a fully formed balloon body and placed into a mold to undergo heating and pressurization.

The described medical balloons like the embodiments depicted in FIGS. 1 and 3 can be used for a number of applications traditionally performed by other compliant, semi-compliant, or non-compliant balloons. Such balloons can be used to perform a PTA procedure, deploy or seat a medical device, deliver a therapeutic agent, deliver RF energy, and/or in any other procedure that would benefit from its properties. When used to deploy, seat, touch-up, or otherwise position medical devices, the described balloon can be used in conjunction with any such devices, such as balloon expandable or self-expanding stents or stent grafts, or other endoluminal devices. In another embodiment, said composite balloon is configured to perform Percutaneous Transluminal Coronary Angioplasty (PTCA). In another embodiment, said composite balloon is configured to treat a coronary stenosis or obstruction. In another embodiment, said composite balloon is configured to treat a peripheral artery stenosis or obstruction.

The balloon of the present disclosure may be employed in any body conduit, cavity, or vessel, including arteries and veins. The balloon embodiments can be used in a variety of medical balloon applications, such as a delivery device for a therapeutic agent to a surrounding tissue or for dilation of vessel, expansion of a stent, and/or touching-up of a previously deployed stent or implanted vascular graft. A body conduit or cavity can include the urinary tract, the intestinal tract, nasal or sinus cavities, neural sheaths, intervertebral regions, bone cavities, the esophagus, intrauterine spaces, pancreatic and bile ducts, rectum, and those previously intervened body spaces that have implanted vascular grafts, stents, prosthesis, or other type of medical implants.

A method of using a medical balloon in accordance with the present disclosure can comprise placing a composite balloon as described herein in a vessel. Once in position, the balloon can be inflated to at least 4 bar, at least 8 bar, at least 12 bar, at least 16 bar, at least 20 bar, at least 25 bar, at least 30 bar, at least 35 bar, or more, or any range or value therebetween.

Having generally described this disclosure, a further understanding can be obtained by reference to certain specific examples illustrated below which are provided for purposes of illustration only and are not intended to be all inclusive or limiting unless otherwise specified.

Testing Methods

It should be understood that although certain methods and equipment are described below, any method or equipment determined suitable by one of ordinary skill in the art may be alternatively utilized.

Mass, Thickness, and Mass Per Unit Area

Membrane samples were die cut to form rectangular sections about 2.54 cm by about 15.24 cm to measure the weight (using a Mettler-Toledo analytical balance model AG204) and thickness (using a snap gauge-Mutitoyo Model, 547-400, 0.5" diameter foot). Using these data, mass per unit area was calculated with the following formula: m/(w*l), in which: mass per unit area (g/cm$^2$), m=mass (g), w=width (cm), and l=length (cm). The average of three measurements was reported.

Bubble Point Test

The isopropyl alcohol bubble point was measured in the following manner: The material was restrained with a circular fixture of 1 inch diameter. The material was subjected to pressurized air at a pressurization rate of about 0.2 psi/sec. The pressure was increased until a stream of bubbles appeared, followed by additional streams of bubbles at similar pressures. The reported values represent the average measurements for five samples.

Matrix Tensile Strength (MTS) of Membranes

Tensile break load was measured using an INSTRON Model 1505 tensile tester equipped with flat-faced grips and a 0.445 kN load cell. The sample dimensions were about 1 inch wide with about 2 inch gauge length tested at about 16.5% per second. For highest strength measurements, the longer dimension of the sample was oriented in the highest strength direction. For the orthogonal MTS measurements, the larger dimension of the sample was oriented perpendicular to the highest strength direction. Each sample was weighed using a Mettler Toledo Scale Model AG204, then the thickness was measured using the snap gauge; alternatively, any suitable means for measuring thickness may be used. The samples can then be tested individually on the tensile tester. Three different sections of each sample were measured. The average of the three maximum loads (i.e., peak force) measurements was reported. The longitudinal and transverse matrix tensile strengths (MTS) were calculated using the following equation: MTS=(maximum load/cross-section area)*(bulk density of PTFE)/(density of the porous membrane), where an example of the bulk density of the PTFE was about 2.2 g/cm$^3$.

Balloon Layer Adhesion Test or "157.5 Degree Peel Test"

The degree of adhesion was quantified in a "Peel Test." This test was performed on an IMASS SP-2100 Slip/Peel Tester wherein the force required to peel apart the layers of the composite 157.50° was measured.

To obtain the test sample, a sheet of layered composite material formed from the composite balloon, the balloon was transversely cut to remove the shoulders and then axially cut along the working length to form a generally rectangular piece of material. Scotch tape was applied around the ends of the sample on the porous layer side, with about 5 mm being covered by the tape and the remainder extending from the edge.

A 6 cm piece of double sided tape was adhered to the center of an IMASS Specimen Test Panel, generally parallel to the long edge. The sheet of material, porous layer side-up, was adhered to the Test Panel with the double-sided tape at the center of the sample. The tape and porous layer from the underlying thermoplastic layer was placed on one end of the sample and the tape was folded over the edge to create a reinforced area to clamp into the IMASS.

A calibrated 5 lb load cell was used on the IMASS, and an adjustment of the transducer gripper was at a 115° angle to the front of the IMASS and a Variable Angle Peel Fixture was installed on to the platen. The test parameters are shown in Table 1. The gripper was positioned and the peeled end secured into the gripper. The sample was peeled such that the sample is extending directly from the gripper in the straight line to the specimen plate forming a 157.5° peel.

TABLE 1

IMASS Test Settings:

| Initial Delay | Averaging | Platen Stop Mode | Force unit | Speed unit | Test Speed |
|---|---|---|---|---|---|
| 0.1 seconds | 10 seconds | Test Time | N | mm/sec | 1.0 mm/sec |

Example 1—Precursor Porous Material

Figure 6A:
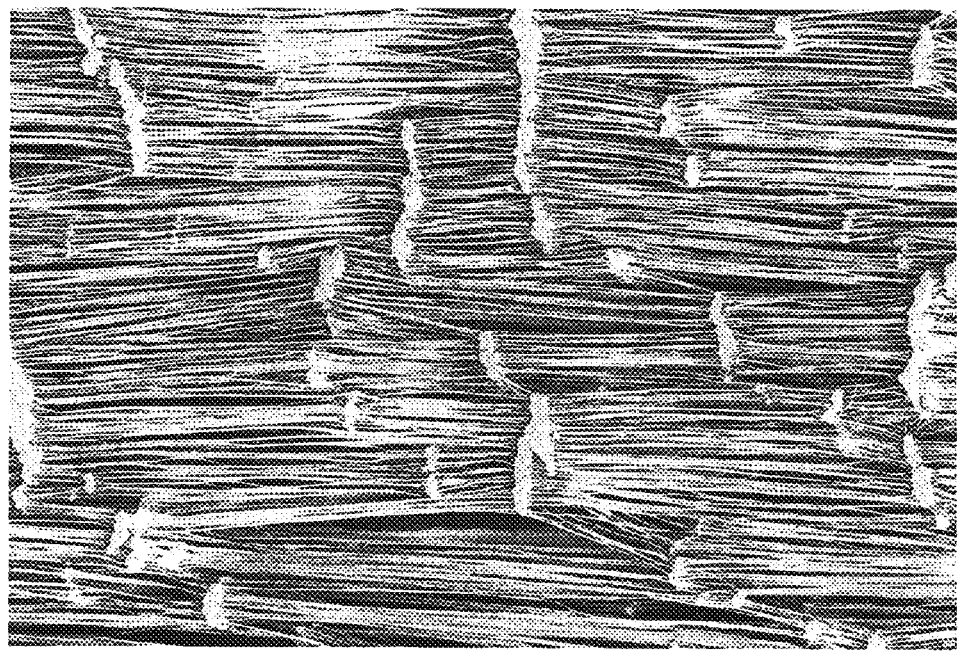
FIGS. 6a and 6b are SEM images of the Example 1 film; an image of each side.
Figure 6B:

An expanded PTFE membrane that was amorphously locked and generally made in accordance with U.S. Pat. No. 3,953,566 had the following properties: thickness of approximately 25 μm, mass per area of approximately 9 g/m$^2$, and a bubble point of approximately 14 kPa. This precursor material had a node and fibril microstructure shown in FIGS. 6a (side 1) and 6b (side 2).

Example 2—Precursor Porous Material

Figure 6C:
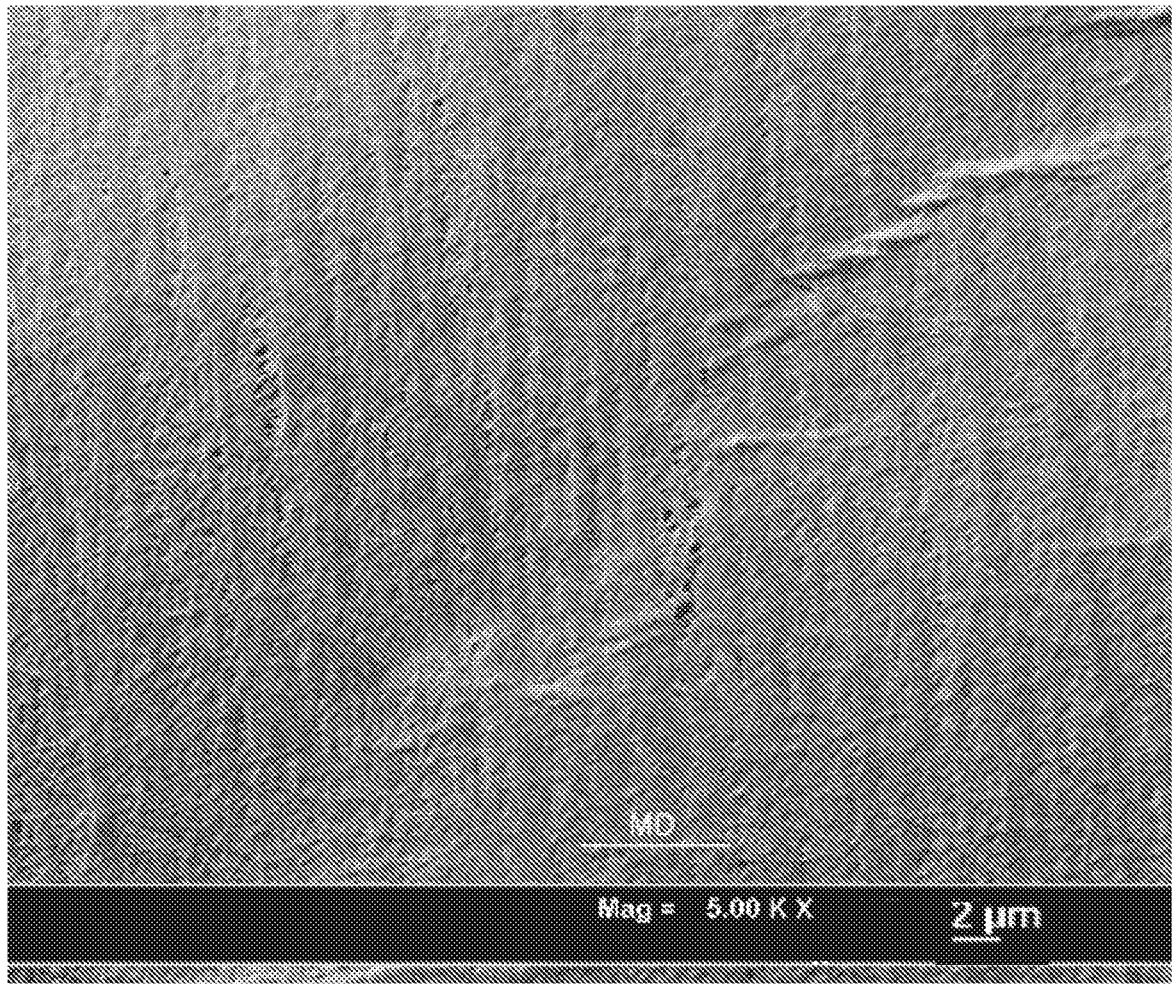
FIG. 6c is an SEM image of the Example 2 film.

An expanded PTFE membrane that was amorphously locked and generally made in accordance with U.S. Pat. No. 7,521,010 had the following properties: thickness of approximately 5 μm, mass per area of approximately 11 g/m$^2$, matrix tensile strength in the strongest direction of approximately 600 MPa, matrix tensile strength in the direction orthogonal to the strongest direction of approximately 230 MPa, strain in maximum load in the strongest direction of approximately 19%, and strain at the maximum load in the transverse direction of approximately 160%. This precursor material had a microstructure shown in FIG. 6c.

For forming circumferentially wrapped tubular members, in some embodiments, the precursor material was cut into a wide sheet or tape, wherein the strongest direction was transverse to the length of the tape and the strongest direction was oriented axially in the formed balloon. In other circumferentially wrapped embodiments, the strongest direction was along the length of the sheet or tape such that the strongest direction was oriented circumferentially in the formed balloon. For forming helically wrapped tubular members, the precursor material was cut into a tape, wherein the strongest direction was along the length of the tape.

Example 3—Construction of a Medical Balloon Comprising a Nominal Diameter of 5 mm with a Smooth Surfaced Mold in Accordance with the Present Disclosure Step 3A: Tubular precursors were formed as follows: The precursor material from Example 1 and Example 2 having a 25 cm width was circumferentially wrapped about a 0.133" mandrel to form 5 layers (or 53 mm of wrapped length). The precursor material was oriented on the mandrel such that the strongest direction was along the length of the tube. This tubular precursor was then thermally treated in an oven at 380° C. for 6 minutes with a protective overwrap and then removed from the oven. Once cooled, the protective overwrap was removed and the tubular precursor was removed from the mandrel.

Step 3B: A nylon balloon extrusion (Grilamid L25 balloon extrusion 0.102"×0.068") was preconditioned in an Interface Catheter Solutions CPS 1000 parison stretcher to form the nylon preform according to the parameters in Table 2.

TABLE 2

Preform Parameters
10 × 62 Nylon 12
Heat - 330° F.

| Left | Run Cycle Setup | Right |
|---|---|---|
| 120 | Speed mm/s | 120 |
| 130 | Distance mm | 130 |
| 7 | Heat Time sec | 7.7 |
| 5. | Dwell Time sec | 5.5 |

Unheated Length 60.0 mm

Step 3C: Two balloon types were made with the tubular precursor prepared in Step 3A. A tubular precursor was slid over the balloon preform prepared in Step 3B and placed into a mold held by an Interface Catheter Solutions Balloon Forming Machine BFM 3310, ensuring both edges of ePTFE were visible from the edge of the end plugs and were not connected to the collet or clamp.

The stretch blow molding programs were run according to the following time, temperature, and pressure parameters of the heat-setting step. A balloon made with the material described in Example 3 exhibited particularly good adhesion.

Time:
    20 Seconds
    45 Seconds
    70 Seconds
Temperature:
    285° F.
    325° F.
    350° F.
Pressure:
    15 Bar
    25 Bar
    35 Bar Step 3D: In some instances, the balloon body was placed upon a catheter and ends of the balloon body were secured to the catheter using a standard balloon catheter thermal bonding technique.

Figure 8A:
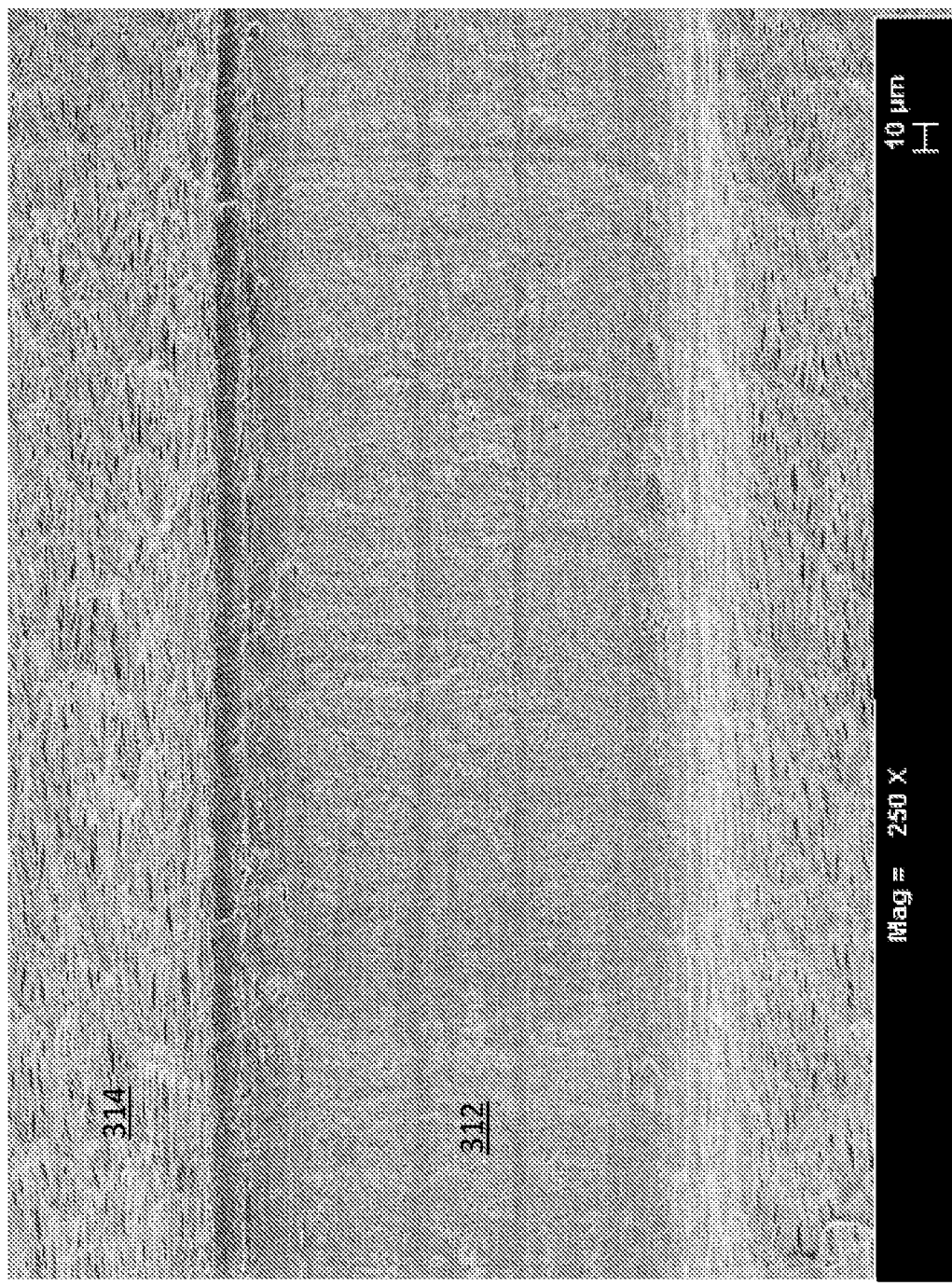
FIG. 8a is an SEM image of a patterned balloon showing a recess region 312 and a protruding region 314 in the ePTFE microstructure.
Figure 8B:
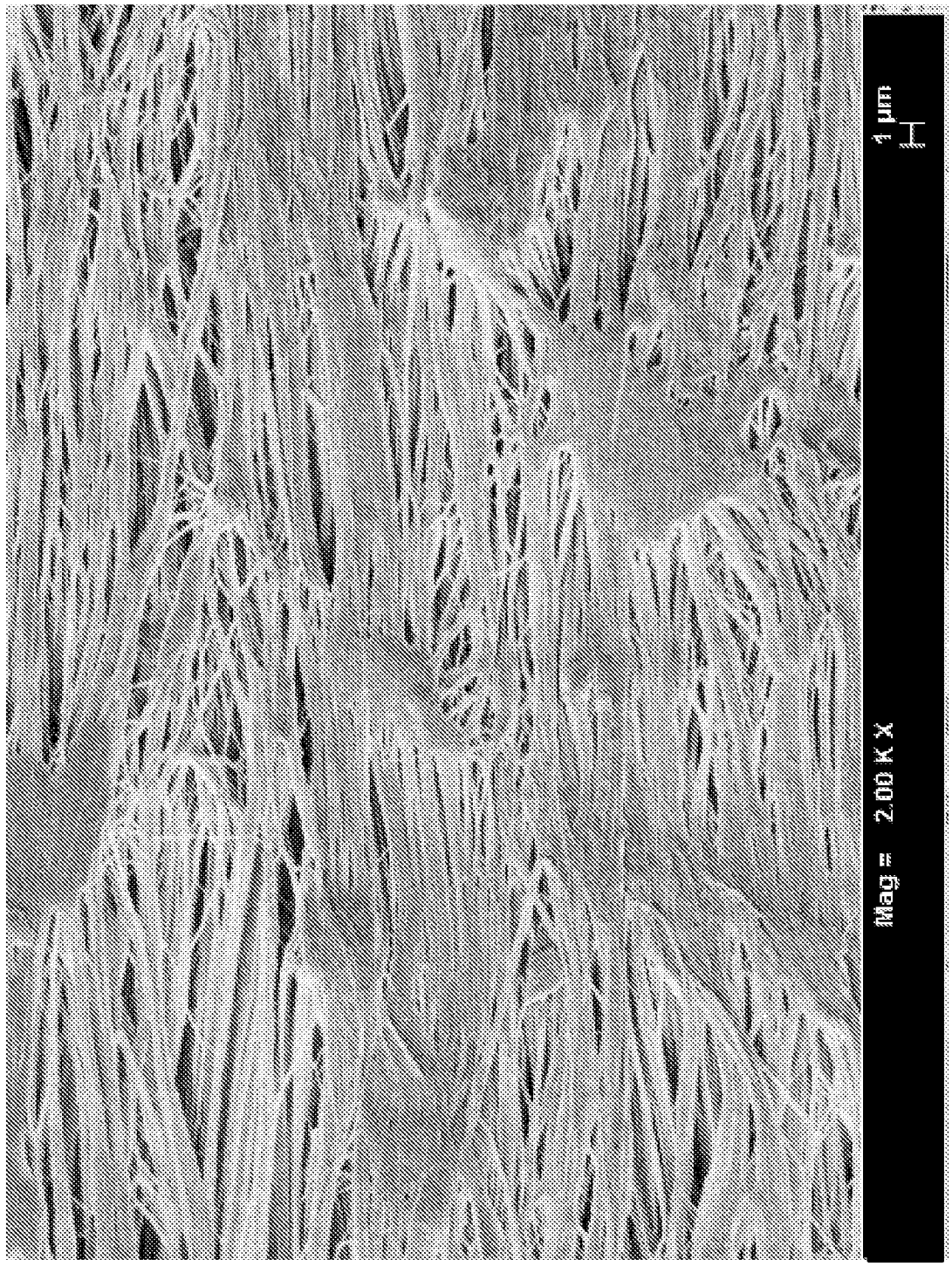
FIG. 8b is an SEM image at a higher magnification showing the microstructure at a protruding region and, conversely.
Figure 8C:
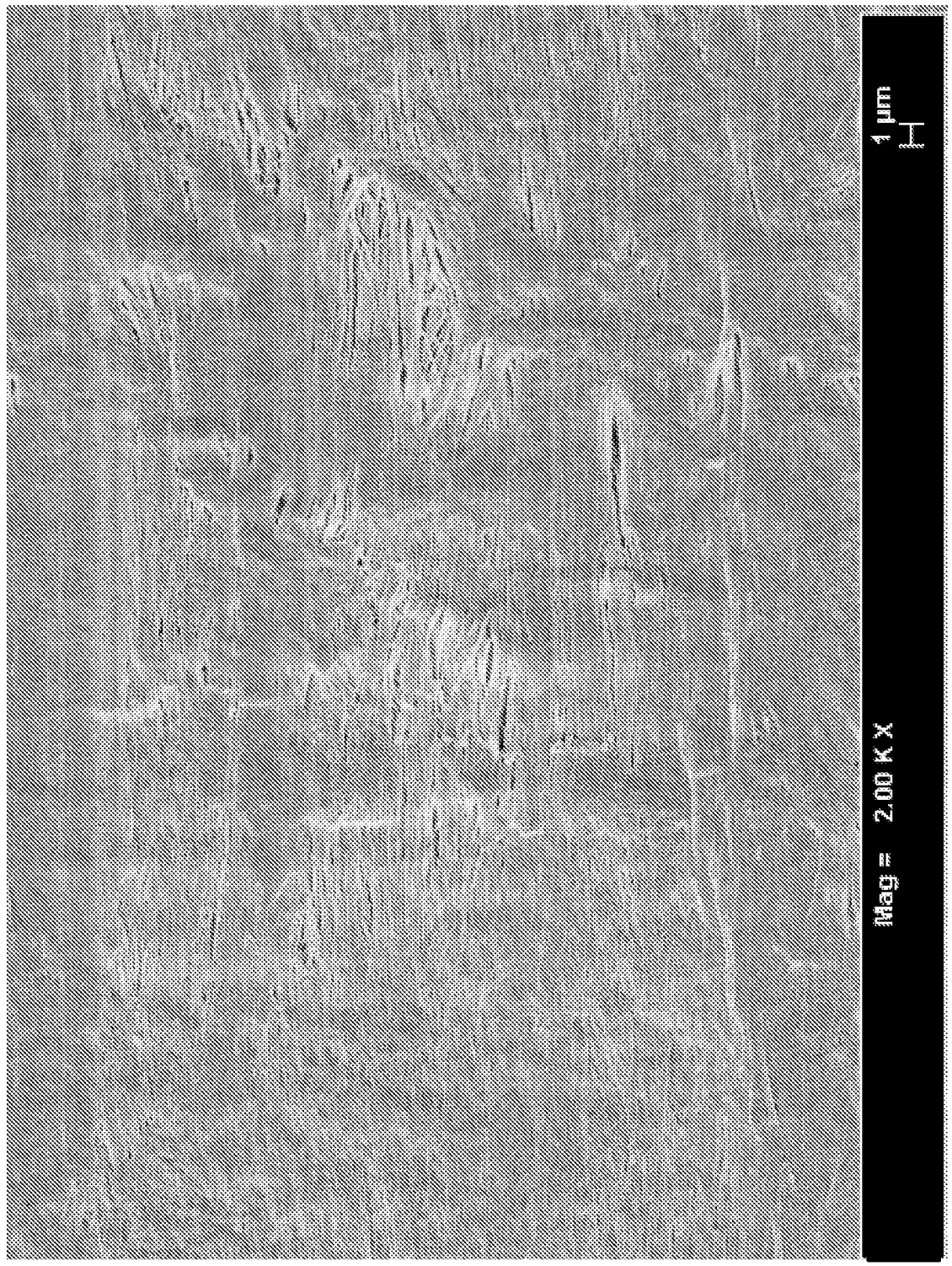
FIG. 8c is an SEM image at a higher magnification showing the microstructure at a recessed region.
Figure 8D:
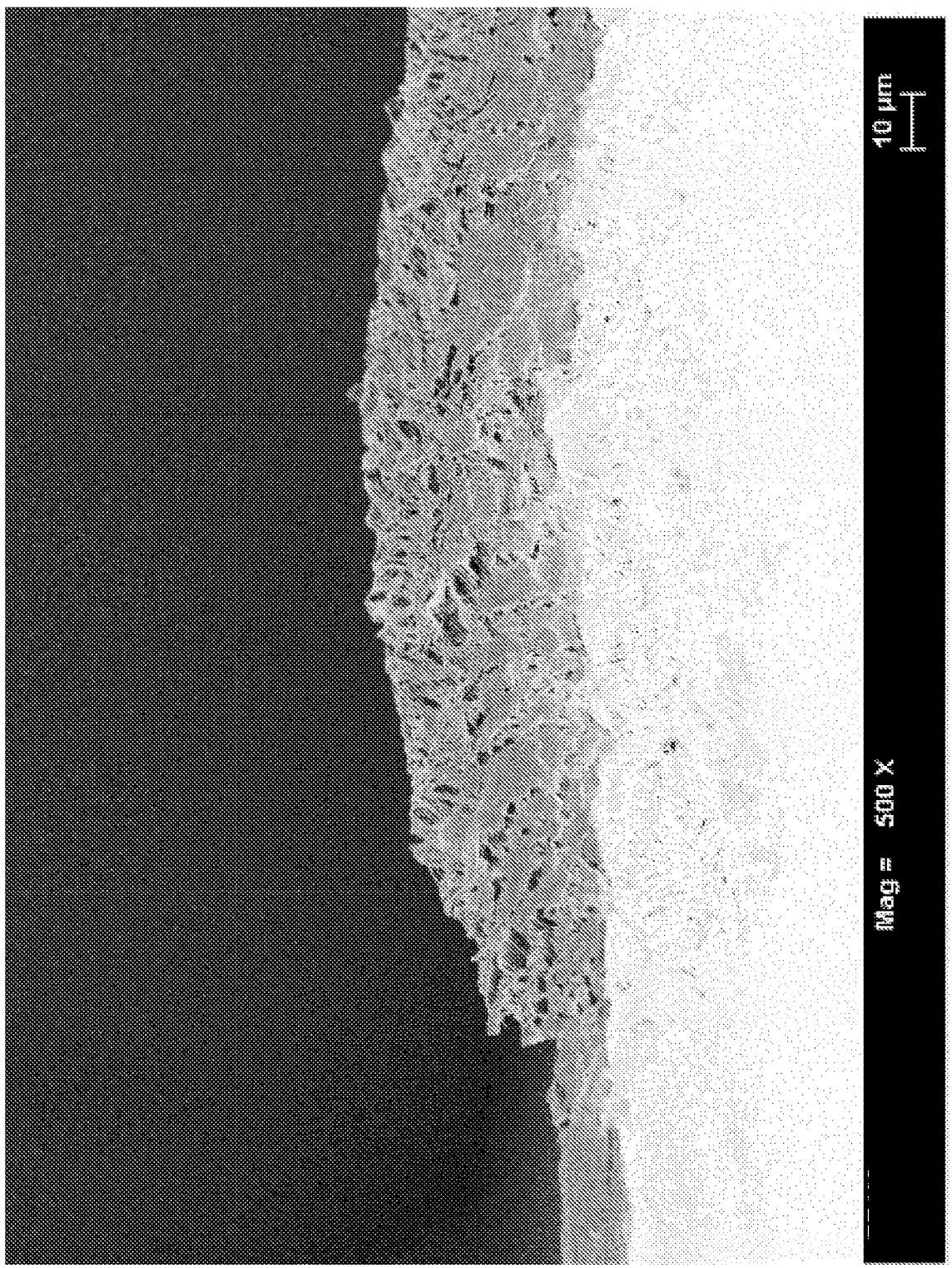
FIG. 8d is an SEM image of the cross-section of the same patterned composite that shows the relative amounts of microstructure thickness, as a portion of a recess is shown on the left-hand side of the image and the protruding region is central in the image.

Example 4—Construction of a Medical Balloon Comprising a Nominal Diameter of 5 mm with a Patterned Mold in Accordance with the Present Disclosure Composite balloons with the tubular precursor of Example 1 were prepared in accordance with Example 3. The mold was a 5×40 mm mold with the general shape depicted in FIG. 2 with longitudinally oriented splines much like that shown and described in FIG. 4. The heat-setting step was conducted at 285° F. for 45 seconds at 25 bar. FIG. 8a is an SEM image of the patterned balloon showing a recess region 312 and a porous region 314 in the ePTFE microstructure. FIG. 8b is an SEM image at a higher magnification showing the microstructure at a protruding region 312 and, conversely, FIG. 8c is an SEM image at a higher magnification showing the microstructure at a recessed region 314. By comparing the two, the relative amounts of collapse in the microstructure can be observed. FIG. 8d is an SEM image of the cross-section of the same patterned composite that also shows the relative amounts of microstructure collapse, as a portion of a recess 312 is shown on the left-hand side of the image and the protruding region 314 is central in the image.

Example 5—Construction of a Medical Balloon Comprising a Nominal Diameter of 5 mm Using a Fully Formed Balloon Body In an alternative embodiment, balloons were prepared in the method that follows: Composite balloons were prepared per Example 3 with a smooth-surfaced 5×40 mm standard mold with the shape depicted in FIG. 2 and a heat-setting step conducted at 285° F. for 45 seconds at 25 bar, and others were prepared per Example 4 with a splined surface.

Step 5A: A tubular precursor was formed as follows: The precursor material from Example 1 and Example 2 having a 25 cm width was circumferentially wrapped about a 0.133" mandrel to form 5 layers (or 53 mm of wrapped length). The precursor material was oriented on the mandrel such that the strongest direction was along the length of the tube. This tubular precursor was then thermally treated in an oven at 380° C. for 6 minutes with a protective overwrap and then removed from the oven. Once cooled, the protective overwrap was removed and the tubular precursor was removed from the mandrel.

Step 5B: A nylon balloon extrusion (Grilamid L25 balloon extrusion 0.102"×0.068") was preconditioned in an Interface Catheter Solutions CPS 1000 parison stretcher to form the nylon preform according to the parameters in Table 2.

TABLE 2

| | Preform Parameters 10 × 62 Nylon 12 Heat - 330° F. | |
|---|---|---|
| Left | Run Cycle Setup | Right |
| 120 | Speed mm/s | 120 |
| 130 | Distance mm | 130 |
| 7 | Heat Time sec | 7.7 |
| 5. | Dwell Time sec | 5.5 |

Unheated Length 60.0 mm

Step 5C: After formation of the balloon body by inflation, one end of the balloon was plugged with a rapid-set adhesive, such as a UV-cure adhesive. A standard compression fitting with an appropriately sized luer fitting was attached to the opposite open end, allowing for pressurization of the balloon by a pressure source.

Step 5D: An instrument such as a one designed for pleating and folding medical balloons was used. For a 10×62 mm balloon, balloon pressure was set to approximately 25 psi. Pleating and compression die temperature was set to 50° C.±5° C. Compression pressure was set at or above 100 psi.

Step 5E: Subsequent to pleating and folding the balloon body, a polymeric layer comprising a porous microstructure, wherein the porous polymeric layer is an outermost layer, was added as an outer layer over the balloon body. After placement over the balloon body, the multi-layer construct was placed back into the balloon mold. The construct was pressurized and heated to the same or similar settings as the previously described heat set settings. The following is a non-limiting example in the formation of a composite balloon body:

Time:
  70 Seconds
Temperature:
  285° F.
  350° F.
Pressure:
  35 Bar

Example 6—Peel Test Study

A 157.5° Peel Test on composite balloon embodiments was prepared in accordance with Example 3 (except for Step 3D) using a 10×62 mm smooth surfaced, standard mold with the shape depicted in FIG. 2. For this Peel Test Study, a 3×3×3 full factorial experiment with the Time, Temperature, and Pressure parameters listed above was conducted, creating 27 possible conditions (summarized in the table of FIG. 7a) with two additional replicates per condition (three total samples per condition) for each balloon type.

Results of a Peel Test, namely, peak kinetic force and average kinetic force, are shown in the Tables in FIGS. 7b(i) and 7b(ii).

Example 7—Construction of Drug-Coated Composite Balloons in Accordance with the Present Disclosure Composite balloons were prepared per Example 3 with a smooth-surfaced 5×40 mm standard mold with the shape depicted in FIG. 2 and a heat-setting step conducted at 285° F. for 45 seconds at 25 bar, and others were prepared per Example 4 with a splined surface. For some balloon samples, the outer balloon surface was further modified to have a plasma treated surface prior to coating with a drug. The ePTFE surface of the balloons was treated with an atmospheric plasma (Tristar Industries) operating at 65% of maximum voltage and 15 SCFH argon flow. A polyethylene (PE) or PTFE packing sheath was placed over the coated balloon segment prior to sterilization. The packing sheath's primary purpose was to maintain the balloon segment at its first diameter. All samples underwent ethylene oxide sterilization.

The outer ePTFE surface of each balloon construct was coated with an 80/20 (dry w/w) paclitaxel/succinic acid coating formulation. Specifically, the balloons were coated by pipetting a known volume of coating solution onto a device while rotating the device at its inflated diameter (5 mm). As solvent from the coating began to evaporate, the balloon was deflated and refolded to its first, un-inflated diameter by applying a slow rate of evacuation to allow the balloon to refold. Coated balloons were dried overnight at room temperature in their folded state. With the exception of the "smooth composite" balloons, the final drug loading on all devices was approximately 3 μg paclitaxel (Ptx) per mm$^2$. Since the smooth composite balloons had a smoother, thinner ePTFE layer (i.e., reduced void space) than the wrapped or splined designs, these devices were coated with less drug dosing (2 μg Ptx per mm2). Thus, more mass of drug was loaded on the balloon construct with the pattern of recesses and protrusions.

The prepared coated balloons (smooth, splined, and wrapped) were also used in an in vivo test to determine the amount of drug that released from the balloon substrate and delivered to the target tissue upon deployment. Prior to performing the in vivo procedure, angiography of each indicated peripheral artery was performed to obtain diameter and length measurements of the treatment site. Diameter measurements at the proximal, midpoint, and distal portions of the treatment site determined the balloon inflation pressure required for appropriate vessel over-sizing. After completion of angiographic sizing, each balloon sample was tracked to the respective target site and deployed according. After tracking to the treatment site, each device was inflated to the required inflation pressure for 60 seconds and subsequently deflated and removed. Post-deployment, the balloon portion of each spent device was cut from the delivery catheter and analyzed for remaining Ptx content.

The artery target sites were also analyzed to determine amount of Ptx delivered to the tissue. For each treated artery, mean Ptx levels in the proximal, treated, and distal segments were calculated by averaging Ptx levels in all tissue sections in the indicated segment.

Based on the analyzed results between the initial amount on the balloon and the amount delivered to the tissue, the efficiency of the dosage was determined (i.e., the percentage of the dose on the balloon that was absorbed in the tissue). Surprisingly, it was observed that the smooth balloons (with a collapsed microstructure) were more efficient at delivering a drug to the tissue than the wrapped or splined designed. Thus, the smooth surfaced balloons can facilitate lower balloon dosing.

Numerous characteristics and advantages have been set forth in the preceding description, including various alternatives together with details of the structure and function of the devices and/or methods. The disclosure is intended as illustrative only and as such is not intended to be exhaustive. For example, embodiments of the present disclosure are described in the context of medical applications but can also be useful in non-medical applications. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A medical balloon comprising a balloon wall defining a chamber and comprising a layered material,
    wherein the layered material comprises a polymer layer adhered to a fluoropolymer layer comprising a porous microstructure,
    wherein the polymer layer and the fluoropolymer layer are in overlying relationship to each other and the fluoropolymer layer is an outermost layer,
    wherein the polymer layer is mechanically adhered to the fluoropolymer layer by a portion of the polymer layer mechanically engaged into the porous microstructure of the fluoropolymer layer at an interface between the polymer layer and the fluoropolymer layer during a blow molding process at a temperature that is less than a melt temperature of the polymer layer, and
    wherein the layered material defines at least one recessed region and at least one non-recessed region on an outer surface of the fluoropolymer layer, the porous microstructure of the fluoropolymer in the at least one recessed region being more compressed than in the non-recessed region such that the at least one recessed region has a higher degree of more collapsed pores relative to the at least one non-recessed region.

2. The medical balloon of claim 1, wherein the polymer layer comprises a seamless polymeric layer and wherein the polymer layer is selected from the group consisting of compliant, semi-compliant and non-compliant material.

3. The medical balloon of claim 1, wherein the at least one recessed region is formed through a blow molding process.

4. The medical balloon of claim 1, wherein the at least one recessed region comprises a porous polymeric layer thickness that is 90% or less relative to a porous polymeric layer thickness of the non-recessed region.

5. The medical balloon of claim 1, wherein the polymer layer is an expanded fluoropolymer.

6. The medical balloon of claim 1, wherein the polymer layer is a polyamide layer.

7. The medical balloon of claim 1, wherein the polymer layer is a thermoplastic polymer.

8. The medical balloon of claim 1, wherein the polymer layer is seamless.

9. The medical balloon of claim 1, wherein the medical balloon is semi-compliant or non-compliant.

10. The medical balloon of claim 1, wherein the medical balloon is compliant.

11. The medical balloon of claim 1, wherein an interface between the polymer layer and the fluoropolymer layer consists of a material of the polymer layer and a material of the fluoropolymer layer.

12. The medical balloon of claim 1, wherein the polymer layer and the fluoropolymer layer are capable of separating with 1 N/m of average kinetic force in a 157 degree Peel Test.

13. The medical balloon of claim 1, wherein the polymer layer and the fluoropolymer layer are capable of separating with 3 N/m of average kinetic force in a 157 degree Peel Test.

14. The medical balloon of claim 1, wherein the polymer layer and the fluoropolymer layer are capable of separating with the occurrence of material failure at a force that is less than the force of the adhesion failure in a 157 degree Peel Test.

15. The medical balloon of claim 1, wherein the medical balloon is inflatable to a pressure greater than 20 bar for a medical balloon of 4 to 8 mm in diameter.

16. The medical balloon of claim 1, further comprising an endovascular medical device disposed about the medical balloon.

17. The medical balloon of claim 1, further comprising a therapeutic agent coated on at least a portion of an outer surface of the balloon wall of the medical balloon.

18. The medical balloon of claim 1, wherein an outer surface of the balloon wall defines a plurality of recesses and a plurality of protrusions.

19. The medical balloon of claim 18, wherein the plurality of recesses and the plurality of protrusions are striated.

20. The medical balloon of claim 19, wherein the plurality of recesses are longitudinally oriented.

21. The medical balloon of claim 18, wherein a maximum width of the plurality of protrusions is between 0.1 mm to 1 mm.

22. The medical balloon of claim 1, wherein the balloon surface defines a plurality of recesses and a plurality of protrusions within the working length of the balloon and wherein the plurality of protrusions cover about 30% to 70% of a total balloon surface area within the working length.

23. The medical balloon of claim 1, wherein the polymer layer is anisotropic.

24. The medical balloon of claim 23, wherein the polymer layer is oriented such that the balloon wall has a lower tensile strength in a longitudinal direction than a radial direction.

25. The medical balloon of claim 23, wherein the polymer layer is oriented such that the balloon wall has a higher tensile strength in a longitudinal direction than a radial direction.

26. The medical balloon of claim 1, where the fluoropolymer layer is isotropic.

27. A medical device comprising a medical balloon, the medical balloon comprising a balloon wall defining a chamber and comprising a layered material,
wherein the layered material comprises an inner polymer layer mechanically adhered to an outer fluoropolymer layer comprising a porous microstructure by a portion of the inner polymer layer mechanically engaged into the porous microstructure of the outer fluoropolymer layer at an interface between the inner polymer layer and the outer fluoropolymer layer during a blow molding process at a temperature that is less than a melt temperature of the inner polymer layer, and a coating layer disposed on an outer surface of the outer fluoropolymer layer, the coating layer comprising a therapeutic agent and an excipient,
wherein the outer fluoropolymer layer is formed from a fluoropolymeric precursor material having a thickness from 5 to 25 μm and a mass per area from 9 to 11 g/m$^2$, and
wherein the layered material defines at least one recessed region and at least one non-recessed region on an outer surface of the outer fluoropolymer layer, the porous microstructure of the fluoropolymer in the at least one recessed region being more compressed than in the non-recessed region such that the at least one recessed region has a higher degree of more collapsed pores relative to the at least one non-recessed region.

28. A medical balloon comprising a balloon wall defining a chamber and comprising a layered material,
wherein the layered material comprises a polymer layer adhered to a fluoropolymer layer comprising a porous microstructure,
wherein the polymer layer and the fluoropolymer layer are in overlying relationship to each other and the fluoropolymer layer is an outermost layer,
wherein the polymer layer is mechanically adhered to the fluoropolymer layer by a portion of the polymer layer mechanically engaged into the porous microstructure of the fluoropolymer layer at an interface between the polymer layer and the fluoropolymer layer during a blow molding process at a temperature that is less than a melt temperature of the polymer layer, and
wherein the layered material defines at least one recessed region on an outer surface of the fluoropolymer layer, and wherein the at least one recessed region comprises a region of more collapsed pores in the fluoropolymer layer relative to a non-recessed region, wherein a higher degree of collapsed pores being less open than a lower degree of collapsed pores.

29. The medical balloon of claim 28, wherein the polymer layer comprises a seamless polymeric layer and wherein the polymer layer is selected from the group consisting of compliant, semi-compliant and non-compliant material.

30. The medical balloon of claim 28, wherein the at least one recessed region is formed through a blow molding process.

31. The medical balloon of claim 28, wherein the at least one recessed region comprises a porous polymeric layer thickness that is 90% or less relative to a porous polymeric layer thickness of the non-recessed region.

32. The medical balloon of claim 28, wherein the polymer layer is an expanded fluoropolymer.

33. The medical balloon of claim 28, wherein the polymer layer is a polyamide layer.

34. The medical balloon of claim 28, wherein the polymer layer is a thermoplastic polymer.

35. The medical balloon of claim 28, wherein the polymer layer is seamless.

36. The medical balloon of claim 28, wherein the medical balloon is semi-compliant or non-compliant.

37. The medical balloon of claim 28, wherein the medical balloon is compliant.

38. The medical balloon of claim 28, wherein an interface between the polymer layer and the fluoropolymer layer consists of a material of the polymer layer and a material of the fluoropolymer layer.

39. The medical balloon of claim 28, wherein the polymer layer and the fluoropolymer layer are capable of separating with 1 N/m of average kinetic force in a 157 degree Peel Test.

40. The medical balloon of claim 28, wherein the polymer layer and the fluoropolymer layer are capable of separating with 3 N/m of average kinetic force in a 157 degree Peel Test.

41. The medical balloon of claim 28, wherein the polymer layer and the fluoropolymer layer are capable of separating with the occurrence of material failure at a force that is less than the force of the adhesion failure in a 157 degree Peel Test.

42. The medical balloon of claim 28, wherein the medical balloon is inflatable to a pressure greater than 20 bar for a medical balloon of 4 to 8 mm in diameter.

43. The medical balloon of claim 28, further comprising an endovascular medical device disposed about the medical balloon.

44. The medical balloon of claim 28, further comprising a therapeutic agent coated on at least a portion of an outer surface of the balloon wall of the medical balloon.

45. The medical balloon of claim 28, wherein an outer surface of the balloon wall defines a plurality of recesses and a plurality of protrusions.

46. The medical balloon of claim 45, wherein the plurality of recesses and the plurality of protrusions are striated.

47. The medical balloon of claim 46, wherein the plurality of recesses are longitudinally oriented.

48. The medical balloon of claim 28, wherein the balloon surface defines a plurality of recesses and a plurality of protrusions within the working length of the balloon and wherein the plurality of protrusions cover about 30% to 70% of a total balloon surface area within the working length.

49. The medical balloon of claim 45, wherein a maximum width of the plurality of protrusions is between 0.1 mm to 1 mm.

50. The medical balloon of claim 28, wherein the polymer layer is anisotropic.

51. The medical balloon of claim 50, wherein the polymer layer is oriented such that the balloon wall has a lower tensile strength in a longitudinal direction than a radial direction.

52. The medical balloon of claim 50, wherein the polymer layer is oriented such that the balloon wall has a higher tensile strength in a longitudinal direction than a radial direction.

53. The medical balloon of claim 28, where the fluoropolymer layer is isotropic.

* * * * *